US011464629B2

(12) United States Patent
Vidlund et al.

(10) Patent No.: US 11,464,629 B2
(45) Date of Patent: *Oct. 11, 2022

(54) ATRIAL POCKET CLOSURES FOR PROSTHETIC HEART VALVES

(71) Applicant: Tendyne Holdings, Inc., St. Paul, MN (US)

(72) Inventors: Zach Vidlund, Minneapolis, MN (US); Michael Evans, Minneapolis, MN (US); Robert M. Vidlund, Forest Lake, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 364 days.

This patent is subject to a terminal disclaimer.

(21) Appl. No.: 16/797,033

(22) Filed: Feb. 21, 2020

(65) Prior Publication Data

US 2020/0188100 A1 Jun. 18, 2020

Related U.S. Application Data

(63) Continuation of application No. 15/992,910, filed on May 30, 2018, now Pat. No. 10,610,358, which is a (Continued)

(51) Int. Cl.
*A61F 2/24* (2006.01)

(52) U.S. Cl.
CPC .... *A61F 2/2418* (2013.01); *A61F 2210/0014* (2013.01); *A61F 2210/0057* (2013.01);
(Continued)

(58) Field of Classification Search
CPC ...... A61F 2/2418; A61F 2/2427; A61F 2/243; A61F 2/2436; A61F 2/2475;
(Continued)

(56) References Cited

U.S. PATENT DOCUMENTS

| 2,697,008 A | 12/1954 | Ross |
| 3,409,013 A | 11/1968 | Berry |

(Continued)

FOREIGN PATENT DOCUMENTS

| CN | 1486161 A | 3/2004 |
| CN | 1961845 A | 5/2007 |

(Continued)

OTHER PUBLICATIONS

US 9,155,620 B2, 10/2015, Gross et al. (withdrawn)
(Continued)

*Primary Examiner* — Alvin J Stewart
(74) *Attorney, Agent, or Firm* — Wei & Sleman LLP

(57) ABSTRACT

A prosthetic heart valve can include an outer frame coupled to an inner frame such that the outer frame can be moved between a first position and a second position in which the outer frame is inverted relative to the inner frame. The inner frame and the outer frame define between them an annular space, and a pocket closure can bound the annular space to form a pocket in which thrombus can form and be retained. The pocket closure can include a stretchable pocket covering that can move from a first position in which the pocket covering has a first length when the outer frame is in the first position relative to the inner frame and a second position in which the pocket covering has a second length greater than the first length when the outer frame is in the second position relative to the inner frame.

20 Claims, 12 Drawing Sheets

Related U.S. Application Data continuation of application No. PCT/US2016/068680, filed on Dec. 27, 2016.

(60) Provisional application No. 62/271,606, filed on Dec. 28, 2015.

(52) U.S. Cl.
CPC .................. *A61F 2220/0075* (2013.01); *A61F 2220/0091* (2013.01); *A61F 2230/0034* (2013.01); *A61F 2230/0069* (2013.01); *A61F 2250/0069* (2013.01)

(58) Field of Classification Search
CPC ............ A61F 2/2457; A61F 2210/0014; A61F 2210/0057; A61F 2250/0069
See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Faheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Monso |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |

(56) References Cited

U.S. PATENT DOCUMENTS

| | | |
|---|---|---|
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Altieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |

(56) References Cited

U.S. PATENT DOCUMENTS

| | | |
|---|---|---|
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 * | 1/2016 | Kovalsky ............ A61F 2/2412 |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,291 B2 * | 3/2016 | Gorman, III .......... A61F 2/2418 |
| 9,289,295 B2 | 3/2016 | Aklog et al. |
| 9,289,297 B2 | 3/2016 | Wilson et al. |
| 9,301,836 B2 * | 4/2016 | Buchbinder .......... A61F 2/2409 |
| 9,345,573 B2 | 5/2016 | Nyuli et al. |
| 9,480,557 B2 | 11/2016 | Pellegrini et al. |
| 9,480,559 B2 * | 11/2016 | Vidlund .............. A61L 27/3625 |
| 9,526,611 B2 | 12/2016 | Tegels et al. |
| 9,532,870 B2 * | 1/2017 | Cooper ................ A61F 2/2418 |
| 9,597,181 B2 * | 3/2017 | Christianson ........ A61F 2/2412 |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,974,647 B2 * | 5/2018 | Ganesan ............... A61F 2/2412 |
| 10,390,952 B2 | 8/2019 | Hariton et al. |
| 10,610,358 B2 * | 4/2020 | Vidlund ................ A61F 2/2418 |
| 11,298,117 B2 * | 4/2022 | Hariton ................ A61B 17/0057 |
| 11,298,227 B2 * | 4/2022 | Vidlund ................ A61F 2/2418 |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Altieri et al. |
| 2005/0075727 A1 | 4/2005 | Wheatley |
| 2005/0080402 A1 | 4/2005 | Santamore et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137688 A1 | 6/2005 | Salahieh et al. |
| 2005/0137690 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |

(56) References Cited

U.S. PATENT DOCUMENTS

| | | |
|---|---|---|
| 2005/0256567 A1 | 11/2005 | Lim et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0188928 A1 | 8/2008 | Salahieh et al. |
| 2008/0208328 A1 | 8/2008 | Antocci et al. |
| 2008/0208332 A1* | 8/2008 | Lamphere .............. A61F 2/2439 623/2.38 |
| 2008/0221672 A1* | 9/2008 | Lamphere .............. A61F 2/2439 623/2.12 |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Mkhatib |
| 2010/0210899 A1 | 8/2010 | Schankereli |
| 2010/0217382 A1 | 8/2010 | Chau et al. |
| 2010/0249489 A1 | 9/2010 | Jarvik |

(56) References Cited

U.S. PATENT DOCUMENTS

| | | |
|---|---|---|
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1* | 11/2010 | McNamara ............ A61B 17/02 604/9 |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1* | 2/2011 | Gabbay ................ A61F 2/2418 623/2.37 |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1* | 8/2012 | Quadri ................ A61F 2/2427 623/2.18 |
| 2012/0283824 A1 | 11/2012 | Lutter et al. |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1* | 7/2013 | Rowe .................... A61F 2/2418 623/2.11 |
| 2013/0190860 A1 | 7/2013 | Sundt, III |
| 2013/0190861 A1* | 7/2013 | Chau .................... A61F 2/2418 623/2.37 |
| 2013/0197622 A1 | 8/2013 | Mitra et al. |
| 2013/0204357 A1 | 8/2013 | Thill et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0304200 A1* | 11/2013 | McLean ................ A61F 2/2418 623/2.18 |
| 2013/0310928 A1* | 11/2013 | Morriss ................ A61F 2/2403 623/2.18 |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0214159 A1 | 7/2014 | Vidlund et al. |
| 2014/0222142 A1* | 8/2014 | Kovalsky .............. A61F 2/2436 623/2.17 |
| 2014/0243966 A1 | 8/2014 | Garde et al. |
| 2014/0249622 A1* | 9/2014 | Carmi .................. A61F 2/2442 623/2.11 |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0358224 A1 | 12/2014 | Tegels et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1* | 4/2015 | Buchbinder .......... A61F 2/2454 623/2.38 |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127096 A1 | 5/2015 | Rowe et al. |
| 2015/0142100 A1* | 5/2015 | Morriss ................ A61F 2/2418 623/2.4 |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1* | 6/2015 | Raanani ................ A61F 2/2436 623/2.11 |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1* | 10/2015 | Quadri ................. A61F 2/2436 623/2.11 |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1* | 12/2015 | Morriss ................ A61F 2/2418 623/2.11 |
| 2015/0351904 A1* | 12/2015 | Cooper ................ A61F 2/2418 623/2.1 |
| 2015/0351906 A1 | 12/2015 | Hammer et al. |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0095700 A1* | 4/2016 | Righini ................ A61F 2/2409 623/2.11 |
| 2016/0106537 A1* | 4/2016 | Christianson ........ A61F 2/2412 623/2.38 |
| 2016/0113764 A1* | 4/2016 | Sheahan ............... A61F 2/2418 623/2.17 |
| 2016/0113766 A1* | 4/2016 | Ganesan .............. A61F 2/2427 623/2.11 |
| 2016/0143736 A1 | 5/2016 | Vidlund |
| 2016/0151155 A1 | 6/2016 | Lutter et al. |
| 2016/0206280 A1 | 7/2016 | Vidlund et al. |
| 2016/0242902 A1 | 8/2016 | Morriss |

(56) References Cited

U.S. PATENT DOCUMENTS

| | | |
|---|---|---|
| 2016/0262879 A1 | 9/2016 | Meiri et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0056166 A1* | 3/2017 | Ratz .................. A61F 2/2418 |
| 2017/0071733 A1* | 3/2017 | Ghione ............... A61F 2/2409 |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0216026 A1* | 8/2017 | Quill .................. A61F 2/2427 |
| 2017/0252153 A1 | 9/2017 | Chau et al. |
| 2017/0266001 A1 | 9/2017 | Vidlund et al. |
| 2017/0312077 A1 | 11/2017 | Vidlund et al. |
| 2017/0333187 A1 | 11/2017 | Hariton et al. |
| 2018/0014930 A1* | 1/2018 | Hariton ............... A61F 2/243 |
| 2018/0021129 A1* | 1/2018 | Peterson ............. A61F 2/2409 623/2.17 |
| 2018/0116798 A1 | 5/2018 | Perszyk |
| 2018/0153687 A1* | 6/2018 | Hariton ............... B23P 15/001 |
| 2018/0206983 A1* | 7/2018 | Noe .................... A61F 2/2412 |
| 2018/0271651 A1* | 9/2018 | Christianson ........ A61F 2/246 |
| 2018/0271653 A1 | 9/2018 | Vidlund et al. |
| 2018/0296341 A1* | 10/2018 | Noe .................... A61F 2/2445 |
| 2018/0325664 A1* | 11/2018 | Gonda ................ A61F 2/2409 |
| 2019/0038404 A1 | 2/2019 | Iamberger et al. |
| 2019/0038405 A1* | 2/2019 | Iamberger ........... B29C 39/10 |
| 2019/0224008 A1 | 7/2019 | Bressloff et al. |
| 2019/0321171 A1* | 10/2019 | Morriss ............... A61F 2/2436 |
| 2019/0321178 A1 | 10/2019 | Tegels |
| 2019/0343627 A1 | 11/2019 | Hariton et al. |
| 2020/0188100 A1* | 6/2020 | Vidlund ............... A61F 2/2418 |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102869317 A | 1/2013 |
| CN | 102869318 A | 1/2013 |
| CN | 102869321 A | 1/2013 |
| CN | 103220993 A | 7/2013 |
| CN | 103974674 A | 8/2014 |
| CN | 102639179 B | 10/2014 |
| CN | 104188737 A | 12/2014 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2009514628 A | 4/2009 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 2000041652 | 7/2000 |
| WO | 2000047139 A1 | 8/2000 |
| WO | 2001035878 A2 | 5/2001 |
| WO | 200149213 A3 | 7/2001 |
| WO | 01 54625 A1 | 8/2001 |
| WO | 2001054624 A1 | 8/2001 |
| WO | 2001056512 A1 | 8/2001 |
| WO | 2001061289 A1 | 8/2001 |
| WO | 2001076510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 2002036048 A1 | 5/2002 |
| WO | 2002041789 A2 | 5/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 03047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006070372 A2 | 7/2006 |
| WO | 2006113906 A1 | 10/2006 |
| WO | 2006127756 A2 | 11/2006 |
| WO | 2007081412 A1 | 7/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013045262 A1 | 4/2013 |
| WO | 2013059747 A1 | 4/2013 |
| WO | 2013096411 A1 | 6/2013 |
| WO | 2013175468 A2 | 11/2013 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2014194178 A1 | 12/2014 |
| WO | 2014210124 A1 | 12/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |

(56) References Cited

FOREIGN PATENT DOCUMENTS

| | | |
|---|---|---|
| WO | 2015138306 A2 | 9/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |

OTHER PUBLICATIONS

Chinese Search Report for Appl. No. 201680072656.1 dated Dec. 26, 2019, 2 pages.
Chinese Search Report for Application No. 201680072656.1 dated Nov. 18, 2020,1 page.
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration In Dilated Hearts," Interactive Cardiovascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves. Description of a New Expandable Aortic Valve and Initial Results with Implantation by Catheter Technique in Closed Chest Pigs," European Heart Journal, 1992, Issue 5, vol. 13, pp. 704-708.
Inoue, K. et al., "Clinical Application of Transvenous Mitral Commissurotomy by a New Balloon Catheter," The Journal of Thoracic and Cardiovascular Surgery, 1984, 87:394-402.

Jin, X. Y. et al., "Aortic Root Geometry and Stentless Porcine Valve Competence," Seminars in Thoracic and Cardiovascular Surgery, Oct. 1999, 11(4):145-150.
Kolata, G., "Device That Opens Clogged Arteries Gets a Failing Grade in a New Study," New York Times [online], <http://www.nytimes.com/1991/01/03/health/device-that-opens-clogged-arteries-gets-a-faili . . . ,>, published Jan. 3, 1991, retrieved from the Internet on Feb. 5, 2016, 3 pages.
L. L. Knudsen et al., "Catheter-Implanted Prosthetic Heart Valves. Transluminal Catheter Implantation of a New Expandable Artificial Heart Valve in the Descending Thoracic Aorta in Isolated Vessels and Closed Chest Pigs," International Journal ofArtificial Organs, 1993, Issue 5, vol. 16, pp. 253-262.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, Georg, et al., Mitral valved stent implantation, European Journal of Cardio-Thoracic Surgery, 2010, vol. 38, pp. 350-355.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic valve," ASAIO Journal, Sep./ Oct. 1996, 42(5):M381-M385.
Orton, C., "Mitralseal: Hybrid Transcatheter Mitral Valve Replacement," Symposium: Small Animal Proceedings, 2011, pp. 311-312.
Pavcnik, M.D., Ph.D., Dusan, et al. "Development and Initial Experimental Evaluation of a Prosthetic Aortic Valve for Transcatheter Placement," Radiology, 1992; 183:151-154.
Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196(11): 173-174.
Rashkind, W. J., "Historical Aspects of Interventional Cardiology: Past, Present, Future," Texas Heart Institute Journal, Dec. 1986, 13(4):363-367.
Reul, H. et al., "The Geometry of the Aortic Root in Health, at Valve Disease and After Valve Replacement," J. Biomechanics, 1990, 23(2):181-191.
Robert C. Ashton Jr., "Development of an Intraluminal Device for the Treatment of Aortic Regurgitation: Prototype and In Vitro Testing System," Journal of Thoracic and Cardiovascular Surgery, 1996, Issue/vol. 112, pp. 979-983.
Rosch, J. et al., "The Birth, Early Years and Future of Interventional Radiology," J Vase Interv Radiol., Jul. 2003, 4:841-853.
Ross, D. N., "Aortic Valve Surgery," Guys Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology, 1990; 176:535-538.
Serruys, P.W. et al., "Stenting of Coronary Arteries. Are we the Sorcerer's Apprentice?," European Heart Journal (1989) 10, 774-782, pp. 37-45, Jun. 13, 1989.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.

(56) References Cited

OTHER PUBLICATIONS

Watt, A.H. et al., "Intravenous Adenosine in the Treatment of the Supraventricular Tachycardia; a Dose-Ranging Study and Interaction with Dipyridamole," British Journal of Clinical Pharmacology (1986), 21, pp. 227-230.

Webb, J. G. et al., "Percutaneous Aortic Valve Implantation Retrograde from the Femoral Artery," Circulation, 2006, 113:842-850.

Wheatley, M.D., David J., "Valve Prostheses," Rob & Smith's Operative Surgery, Fourth Edition, 1986, pp. 415-424, Butterworths 1986.

Yoganathan, A. P. et al., "The Current Status of Prosthetic Heart Valves," In Polymetric Materials and Artificial Organs, Mar. 20, 1983, pp. 111-150, American Chemical Society.

"Shape Memory Alloys," Retrieved from the Internet: <http://webdocs.cs.ualberta.ca/~database/MEMS/sma.html>, Feb. 5, 2016, 3 pages.

International Search Report and Written Opinion for International Application No. PCT/US2016/068680, dated Jun. 16, 2017, 18 pages.

\* cited by examiner

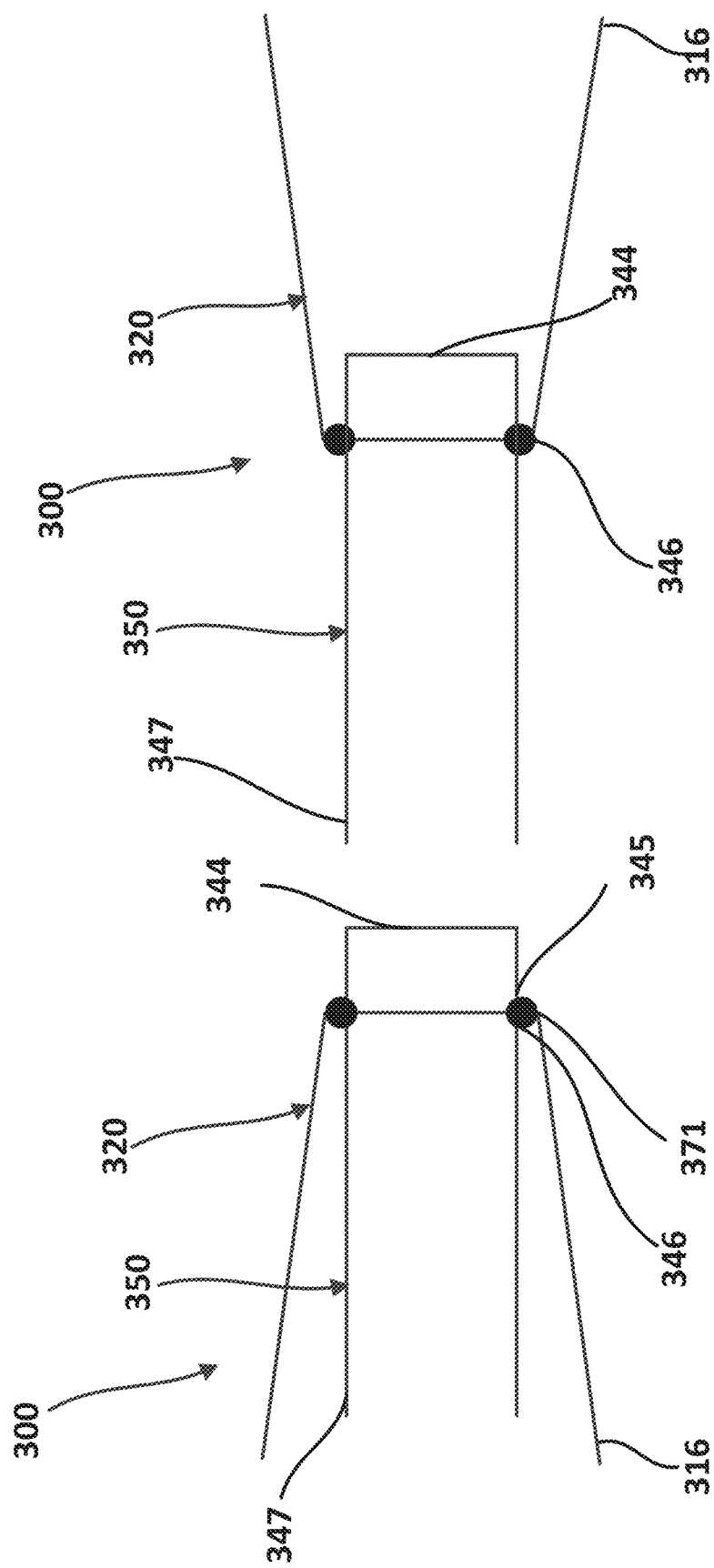

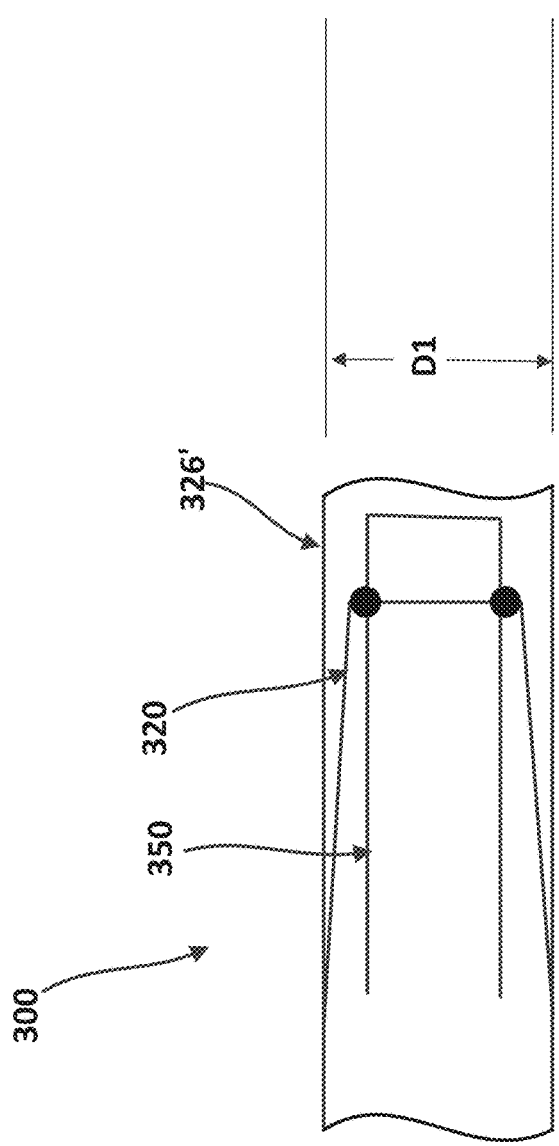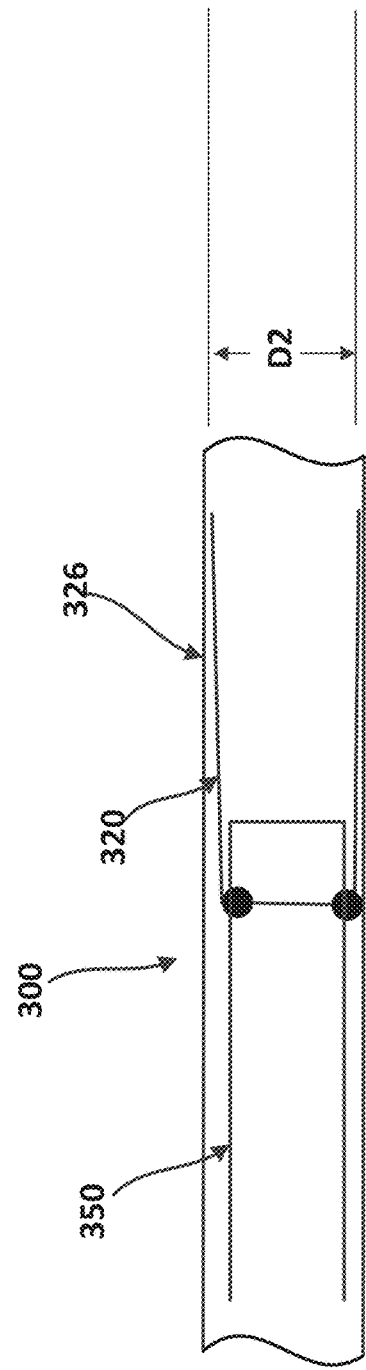

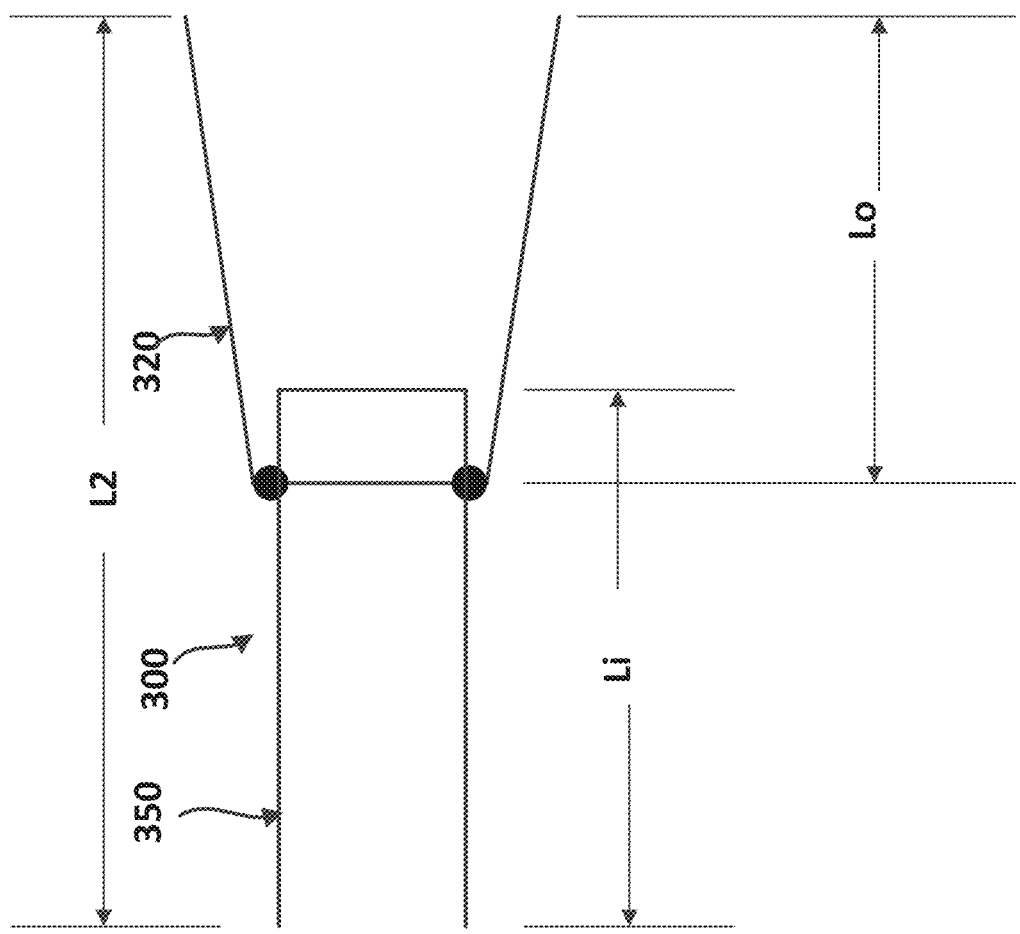
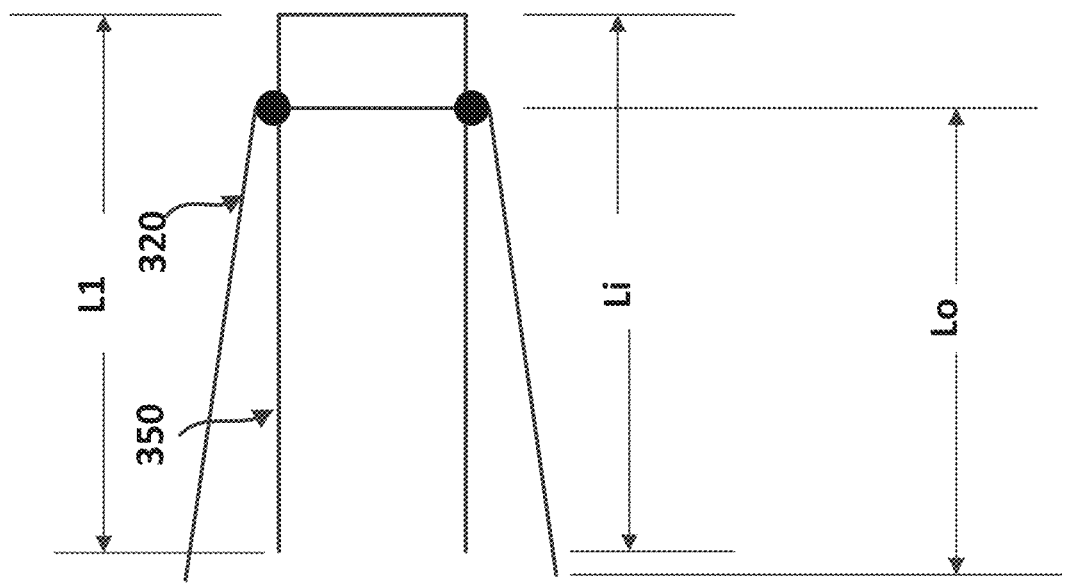
FIG. 7A
FIG. 7B

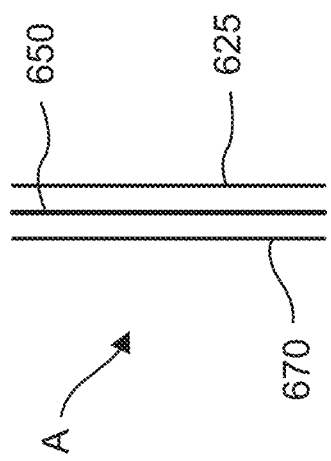
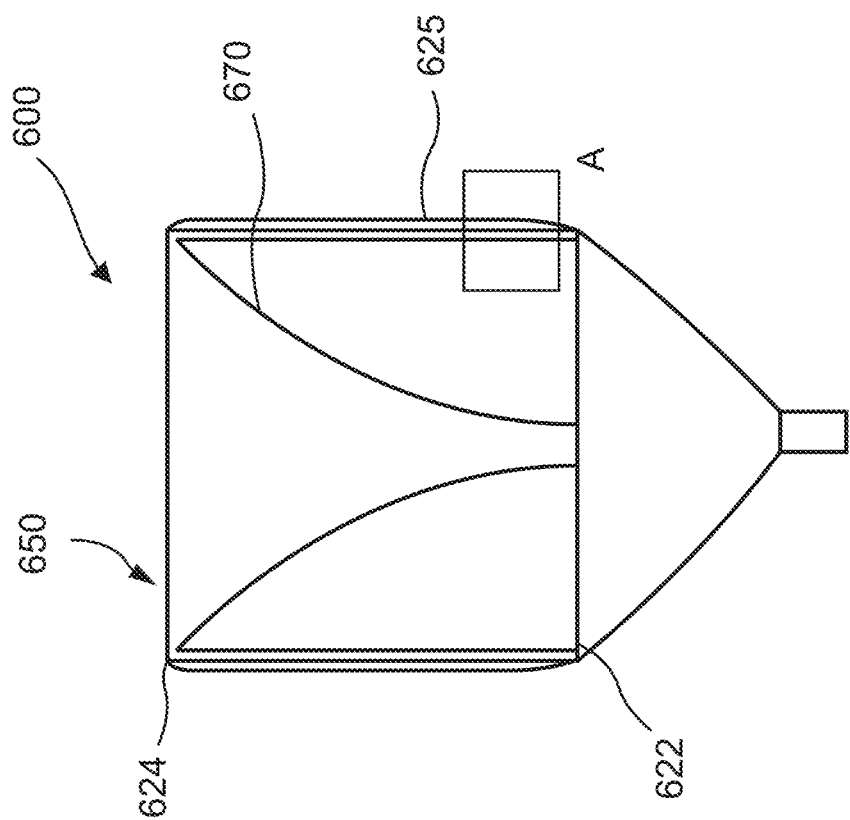

ATRIAL POCKET CLOSURES FOR PROSTHETIC HEART VALVES

CROSS-REFERENCE TO RELATED APPLICATIONS

This application is a continuation of U.S. patent application Ser. No. 15/992,910, filed May 30, 2018, which is a continuation of International Application No. PCT/US2016/068680, filed on Dec. 27, 2016, which claims priority to and the benefit of U.S. Provisional Patent Application No. 62/271,606, entitled "Atrial Pocket Closures for Prosthetic Heart Valves," filed Dec. 28, 2015, each of the disclosures of which is incorporated herein by reference in its entirety.

This application is related to International Application No. PCT/US14/44047, filed Jun. 25, 2014, which is a continuation-in-part of U.S. patent application Ser. No. 14/155,535, filed Jan. 15, 2014, and claims priority to and the benefit of U.S. Provisional Application No. 61/839,237, filed Jun. 25, 2013 and U.S. Provisional Application No. 61/840,313, filed Jun. 27, 2013. The disclosures of the foregoing applications are incorporated herein by reference in their entirety.

BACKGROUND

Prosthetic heart valves, including those for insertion into atrioventricular valves (tricuspid and mitral valves) are susceptible to various problems, including problems with insufficient articulation and sealing of the valve within the native valve annulus, pulmonary edema due to poor atrial drainage, perivalvular leaking around the install prosthetic valve, lack of a good fit for the prosthetic valve within the native valve annulus, atrial tissue erosion, excess wear on the Nitinol structures, interference with the aorta at the anterior side of the mitral annulus, lack of customization, and thrombus formation, to name a few. Accordingly, there is a need for a prosthetic heart valve that can address some or all of these problems.

Moreover, there are a variety of different delivery approaches for delivering and deploying a prosthetic heart valve into atrioventricular valves and depending on the delivery approach the desired features and structure of a prosthetic heart valve can vary. For example, in transvascular delivery of a prosthetic heart valve it is desirable to have a prosthetic heart valve that can have an expanded configuration for implantation within the heart and a collapsed or compressed configuration that has a sufficiently small outer perimeter or diameter to allow the prosthetic heart valve to be placed in a relatively small delivery catheter or sheath. In such embodiments of a prosthetic heart valve, it is also desirable for features of the prosthetic heart valve, such as those described above, to be maintained.

SUMMARY

In some embodiments, a prosthetic heart valve can include an outer frame coupled to an inner frame such that the outer frame can be moved between a first position relative to the inner frame and a second position relative to the inner frame in which the outer frame is inverted relative to the inner frame. The inner frame and the outer frame define between them an annular space. In some embodiments, a pocket closure bounds the annular space to form a pocket in which thrombus can form and be retained. The pocket closure can include a stretchable pocket covering that can move from a first position in which the pocket covering has a first length when the outer frame is in the first position relative to the inner frame and a second position in which the pocket covering has a second length greater than the first length when the outer frame is in the second position relative to the inner frame.

BRIEF DESCRIPTION OF THE DRAWINGS

FIGS. 6A and 6B are schematic illustrations of a portion of a prosthetic heart valve, according to an embodiment, shown in a first configuration and a second configuration, respectively.

FIGS. 6C and 6D are schematic illustrations of the portion of the prosthetic heart valve of FIGS. 6A and 6B, respectively, shown disposed within a delivery sheath.

FIGS. 7A and 7B are schematic illustrations of the portion of a prosthetic heart valve of FIGS. 6A and 6B, shown in the first configuration and the second configuration, respectively.

FIG. 10A is a cross-sectional side view of a prosthetic heart valve, according to another embodiment.

FIG. 10B is an enlarged view of encircled area A in FIG. 10A.

DETAILED DESCRIPTION

Figure 1A:
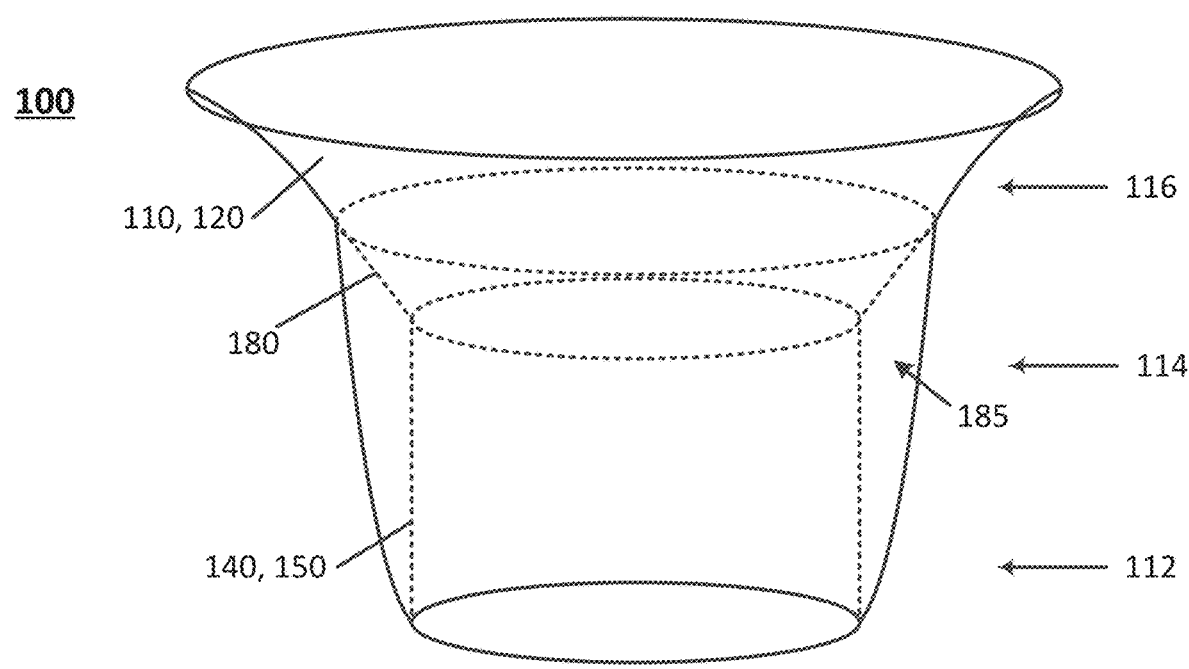
FIGS. 1A and 1B are a schematic perspective view and a side cross-sectional view, respectively, of a prosthetic heart valve, according to an embodiment.

Prosthetic heart valves are described herein that include an outer frame coupled to an inner frame. The outer frame and the inner frame define between them an annular space, and a pocket closure bounds the annular space to form a pocket in which thrombus can form and be retained. In some embodiments, a prosthetic heart valve includes an outer frame coupled to an inner frame such that the outer frame can be moved between a first position relative to the inner frame and a second position relative to the inner frame in which the outer frame is inverted relative to the inner frame. In such an embodiment, the pocket closure can include a stretchable pocket covering that can move from a first position in which the pocket covering has a first length when the outer frame is in the first position relative to the inner frame and a second position in which the pocket covering has a second length greater than the first length when the outer frame is in the second position relative to the inner frame.

In some embodiments, prosthetic heart valves described herein can be configured to be moved to an inverted configuration for delivery of the prosthetic valve to within a heart of a patient. For example, in some embodiments, a prosthetic valve includes an outer frame that can be inverted relative to an inner frame when the prosthetic valve is in a biased expanded configuration. The prosthetic mitral valve can be formed with, for example, a shape-memory material. After inverting the outer frame, the prosthetic valve can be inserted into a lumen of a delivery sheath such that the prosthetic valve is moved to a collapsed configuration.

The delivery sheath can be used to deliver an inverted prosthetic valve as described herein to within a patient's heart using a variety of different delivery approaches for delivering a prosthetic heart valve (e.g., prosthetic mitral valve) where the inverted prosthetic valve would enter the heart through the atrium of the heart. For example, the prosthetic valves described herein can be delivered using a transfemoral delivery approach as described in International Application No. PCT/US15/14572 (the '572 PCT application) incorporated by reference above or via a transatrial approach, such as described in U.S. Provisional Patent Application Ser. No. 62/220,704, entitled "Apparatus and Methods for Transatrial Delivery of Prosthetic Mitral Valve," filed Sep. 18, 2015 ("the '704 provisional application"), and described in U.S. patent application Ser. No. 15/265,221 filed Sep. 14, 2016 (the '221 application"), the entire disclosures of which are incorporated herein by reference in their entirety. In another example, an inverted valve as described herein could be delivered via a transjugular approach, via the right atrium and through the atrial septum and into the left atrium, as described in the '221 application. The prosthetic valves described herein can also be delivered apically if desired. After the delivery sheath has been disposed within the left atrium of the heart, the prosthetic mitral valve is moved distally out of the delivery sheath such that the inverted outer frame reverts and the prosthetic valve assumes its biased expanded configuration. The prosthetic mitral valve can then be positioned within a mitral annulus of the heart.

Figure 1B:
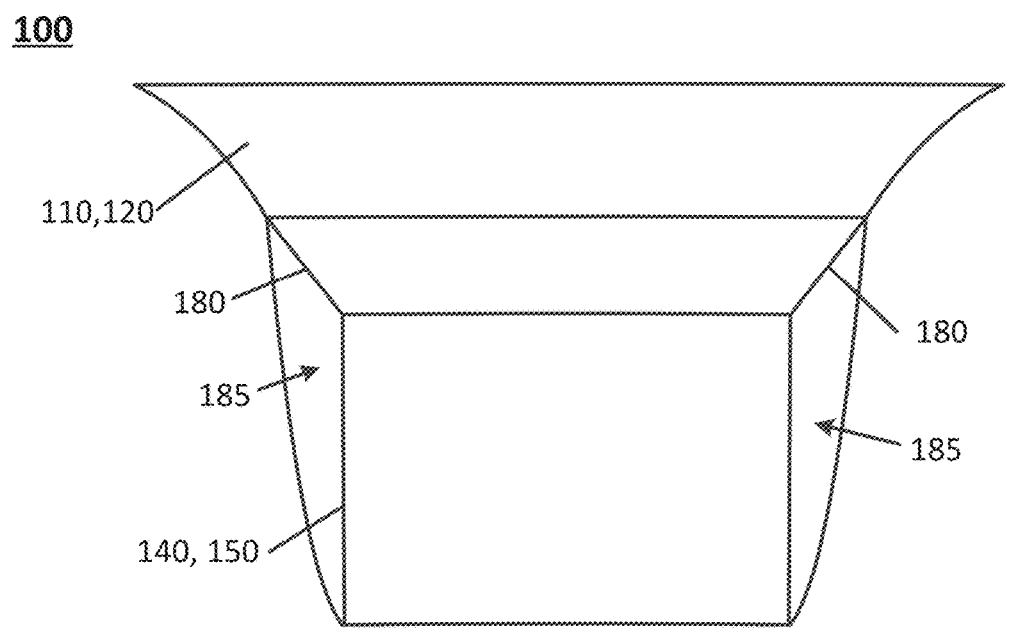

A schematic representation of a prosthetic heart valve 100 is shown in FIGS. 1A and 1B. Prosthetic heart valve 100 (also referred to as "prosthetic valve" or "valve") is designed to replace a damaged or diseased native heart valve such as a mitral valve. Valve 100 includes an outer frame assembly 110 and an inner valve assembly 140 that is coupled to the outer frame assembly.

Although not separately shown in the schematic illustration of outer frame assembly 110 in FIGS. 1A and 1B, outer fame assembly 110 may be formed of an outer frame 120, and can be covered on all or a portion of its outer face with an outer covering (not shown), and covered on all or a portion of its inner face by an inner covering (not shown). An embodiment of a prosthetic valve showing the inner and outer coverings is described below with respect to FIGS. 3-5. In some embodiments, the outer frame assembly 110 can include a covering on only an outer face or only an inner face of the outer frame 120. In some embodiments, there can be more than one layer of covering on the inner face and/or the outer face of the outer frame 120. The inner and outer coverings of the outer frame assembly 110 can completely cover the inner face and/or outer face of the outer frame 120 or can partially cover the inner face and/or the outer face of the outer frame 120. In some embodiments, the outer frame assembly 110 may not include a covering on the inner face or the outer face of the outer frame 120. For example, in some embodiments, the outer frame assembly 110 can include no material or covering on an inner face of the outer frame 120 and two layers or coverings disposed on an outer face of the outer frame 120. In such an embodiment, a first layer or covering can be, for example, a tissue that fully covers the outer face of the outer frame 120 and the outermost layer or covering can be a thin polyester that covers only a portion of the outer frame 120. For example, the outermost covering can cover one or two rows of cells of a cuff portion of the outer frame 120.

Outer frame 120 can provide several functions for prosthetic heart valve 100, including serving as the primary structure, as an anchoring mechanism and/or an attachment point for a separate anchoring mechanism to anchor the valve to the native heart valve apparatus, a support to carry inner valve assembly 140, and/or a seal to inhibit paravalvular leakage between prosthetic heart valve 100 and the native heart valve apparatus.

Outer frame 120 is preferably formed so that it can be deformed (compressed and/or expanded) and, when released, return to its original (undeformed) shape. To achieve this, outer frame 120 is preferably formed of materials, such as metals or plastics, that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may be used.

Outer frame 120 is preferably formed from a laser cut, thin-walled tube of Nitinol®. The laser cuts form regular cutouts in the thin Nitinol® tube. The tube can be expanded radially, placed on a mold or mandrel of the desired shape, heated to the martensitic temperature, and quenched. The treatment of the frame in this manner will form an open lattice frame structure, and may have a flared end or cuff at the atrium end portion 116 of outer frame 120. Outer frame 120 thus has shape memory properties and will readily revert to the memory shape at the calibrated temperature. Alternatively, outer frame 120 may be constructed from braided wire or other suitable material.

Figure 2A:
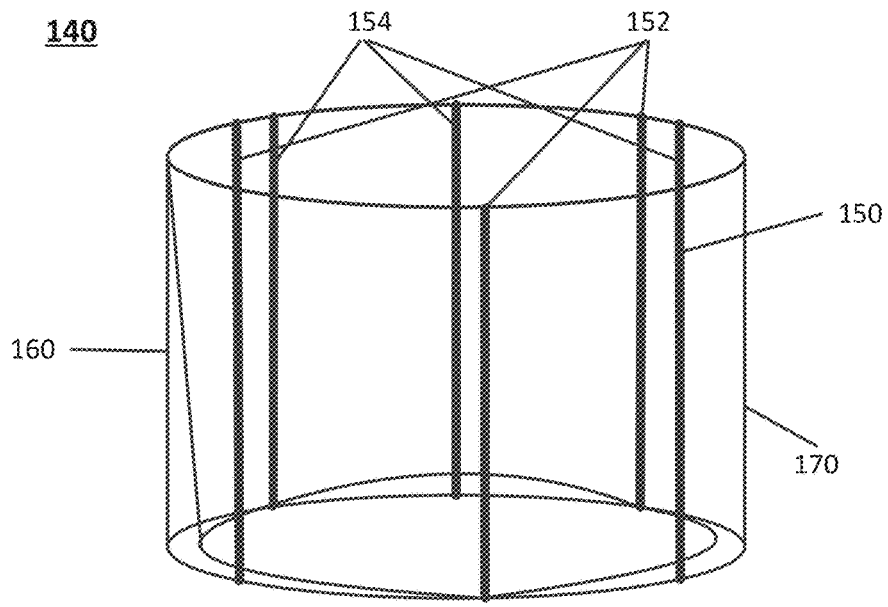
FIG. 2A is a schematic perspective view, of an inner valve assembly of the prosthetic heart valve of FIGS. 1A and 1B.
Figures 2B, 2C:
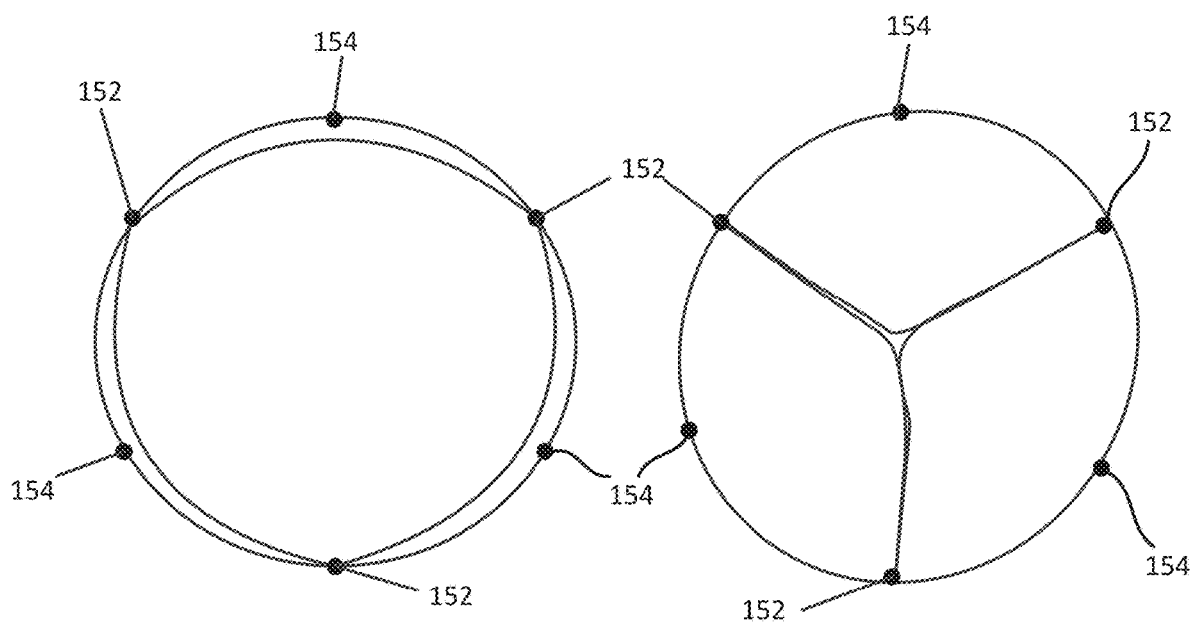
FIGS. 2B and 2C are schematic top views of the inner valve of FIG. 2A, shown in a first configuration and a second configuration, respectively.

Inner valve assembly 140 is shown schematically in more detail in FIGS. 2A-2C. Inner valve assembly 140 can include an inner frame 150, an outer covering 160, and leaflets 170. In the simplified form shown schematically in FIG. 2A, inner frame 150 includes six axial posts or frame members that support outer covering 160 and leaflets 170. Leaflets 170 are attached along three of the posts, shown as commissure posts 152 in FIG. 2A, and outer covering 160 is attached to the other three posts, 154 in FIG. 2A, and optionally to commissure posts 152. The outer covering 160 can be attached to an inner face of the inner frame 150 or to an outer face of the inner frame 150. As shown schematically in FIG. 2A, each of outer covering 160 and leaflets 170 are formed of approximately rectangular sheets of material, which are joined together at their upper, or atrium end. The lower, ventricle end of outer covering 160 may be joined to the inner covering (not shown) of outer frame assembly 110 (not shown in FIG. 2A), and the lower, ventricle end of leaflets 170 may form free edges, though coupled to the lower ends of commissure posts 152. In some embodiments, the covering 160 and leaflets 170 can be formed from a single rectangular sheet of material, then folded over and trimmed to the shape of the inner frame, staying connected at the top of the inner frame where the material is folded over. In some embodiments, the covering 160 and/or the leaflets 170 can be formed from material having a shape other than rectangular, such as from a semi-circular piece of material, or can be laser cut to the shape of the inner frame.

As shown in FIGS. 2B and 2C, leaflets 170 are movable between a first or open configuration (FIG. 2B), and a second or closed configuration (FIG. 2C) in which the leaflets 170 coapt, or meet in sealing abutment.

At the lower, or ventricle end, leaflets 170 may have a smaller outer perimeter than outer covering 160. Thus, the free lower edges of the leaflets 170, between commissure posts 152 (each portion of leaflets 170 between adjacent commissure posts being referred to as a "belly" of leaflets 170) are spaced radially from the lower edge of outer covering 160. This radial spacing facilitates movement of the leaflets from the open position in FIG. 2B to the closed position in FIG. 2C, as the counter flow of blood from the ventricle to the atrium during systole can catch the free edges of the bellies and push the leaflets closed.

The outer covering and the inner covering of outer frame assembly 110, outer covering 160 and leaflets 170 may be formed of any suitable material, or combination of materials. In some embodiments, the outer covering and the inner covering of outer frame assembly 110, outer covering 160 and leaflets 170 may be formed of a tissue. In some embodiments, the tissue is optionally a biological tissue, such as a chemically stabilized tissue from a heart valve of an animal, such as a pig, or pericardial tissue of an animal, such as cow (bovine pericardium) or sheep (ovine pericardium) or pig (porcine pericardium) or horse (equine pericardium). Examples of suitable tissue include that used in the products Duraguard®, Peri-Guard®, and Vascu-Guard®, all products currently used in surgical procedures, and which are marketed as being harvested generally from cattle less than 30 months old. Alternatively, valve leaflets 170 may optionally be made from pericardial tissue or small intestine submucosal tissue.

Synthetic materials, such as polyurethane or polytetrafluoroethylene, may also be used for valve leaflets 170. Where a thin, durable synthetic material is contemplated, e.g. for the outer covering or the inner covering of outer frame assembly 110, synthetic polymer materials such as, for example, expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

In another embodiment, valve leaflets 170 may optionally have a surface that has been treated with (or reacted with) an anti-coagulant, such as, without limitation, immobilized heparin. Such currently available heparinized polymers are known and available to a person of ordinary skill in the art.

As shown in FIGS. 1A, 1B, and 2A, inner valve assembly 140 may be substantially cylindrical, and outer frame assembly 110 may be tapered, extending from a smaller diameter (slightly larger than the outer diameter of inner valve assembly 140) at a lower, ventricle portion 112 (where it is coupled to inner valve assembly 140) to a larger diameter, atrium portion 116, with an intermediate diameter, annulus portion 114 between the atrium and ventricle portions, 112 and 116, respectively.

A tapered annular space or pocket 185 (also referred to herein as "atrial pocket") is thus formed between the outer surface of inner valve assembly 140 and the inner surface of outer frame assembly 110, open to the atrium end of valve assembly 100. When valve assembly 100 is disposed in the annulus of a native heart valve, blood from the atrium can move in and out of pocket 185. The blood can clot, forming thrombus. To enhance clotting, ingrowth of tissue into the surfaces of valve 100, and produce other benefits, the pocket can be covered, or enclosed, by a pocket closure 180 (also referred to as an "atrial pocket closure").

Pocket closure 180 can be formed at least in part of any suitable material that is sufficiently porous to allow blood, including particularly red blood cells, to enter pocket 185, but is not so porous as to allow undesirably large thrombi to leave the pocket 185. For example, pocket closure 180 may be formed at least in part from a woven or knit polyester fabric with apertures less than 160µ, and preferably between 90µ and 120µ. In some embodiments, the pocket closure 180 can be formed at least in part from a braided Nitinol material that has a desired porosity. In some embodiments, the pocket closure 180 can be formed at least in part from a braided tubular Nitinol material. It is not necessary for the entirety of pocket closure 180 to be formed of the same material, with the same porosity. For example, some portions of pocket closure 180 may be formed of a less porous, or blood impermeable, material and other portions formed of material of the porosity range noted above. It is also contemplated that a portion of the outer frame assembly 110 or the inner valve assembly 140 may be formed with an aperture that communicates with pocket 180, covered by a closure formed of material having the desired porosity, thus providing another path by which blood may enter, but thrombi are prevented from leaving, atrial pocket 185.

The outer surface of inner valve assembly 110, and/or the inner surface of outer frame assembly 140, need not by circular in cross-section as shown schematically in FIGS. 1A and 1B, but may be of non-constant radius at a given location along the central axis of valve 100. Thus, pocket 185 may not be of constant cross-section, and may not be continuous, but rather may be formed in two or more fluidically isolated, partially annular volumes. Similarly, pocket closure 180 need not be shaped as a ring with constant width as shown schematically in FIGS. 1A and 1B, but rather can be a continuous ring of varying width, a more complicated continuous shape, or may be formed in multiple, discrete sections. In some embodiments, the pocket closure 180 can be formed as a tubular member defining an interior region.

Pocket closure 180 serves to trap and/or slow the flow of blood within pocket 185, which can increase formation and retention of thrombus in pocket 185. It also promotes active in-growth of native tissue into the several coverings of prosthetic heart valve 100, further stabilizing valve 100 in the native heart valve. The material forming the outer covering of inner valve assembly 140 can also be hardened or stiffened, providing better support for leaflets 170. Also, a mass of thrombus filling pocket 185 can serve as potting for inner valve assembly 140, further stabilizing the valve assembly. Greater stability for inner valve assembly 140 can provide more reliable coaption of valve leaflets 170, and thus more effective performance. The mass of thrombus can also stabilize the outer frame assembly 110 after it has been installed in, and flexibly conformed to, the native valve apparatus. This can provide a more effective seal between prosthetic heart valve 100 and the native valve apparatus, and reduce perivalvular leakage.

Figure 3:
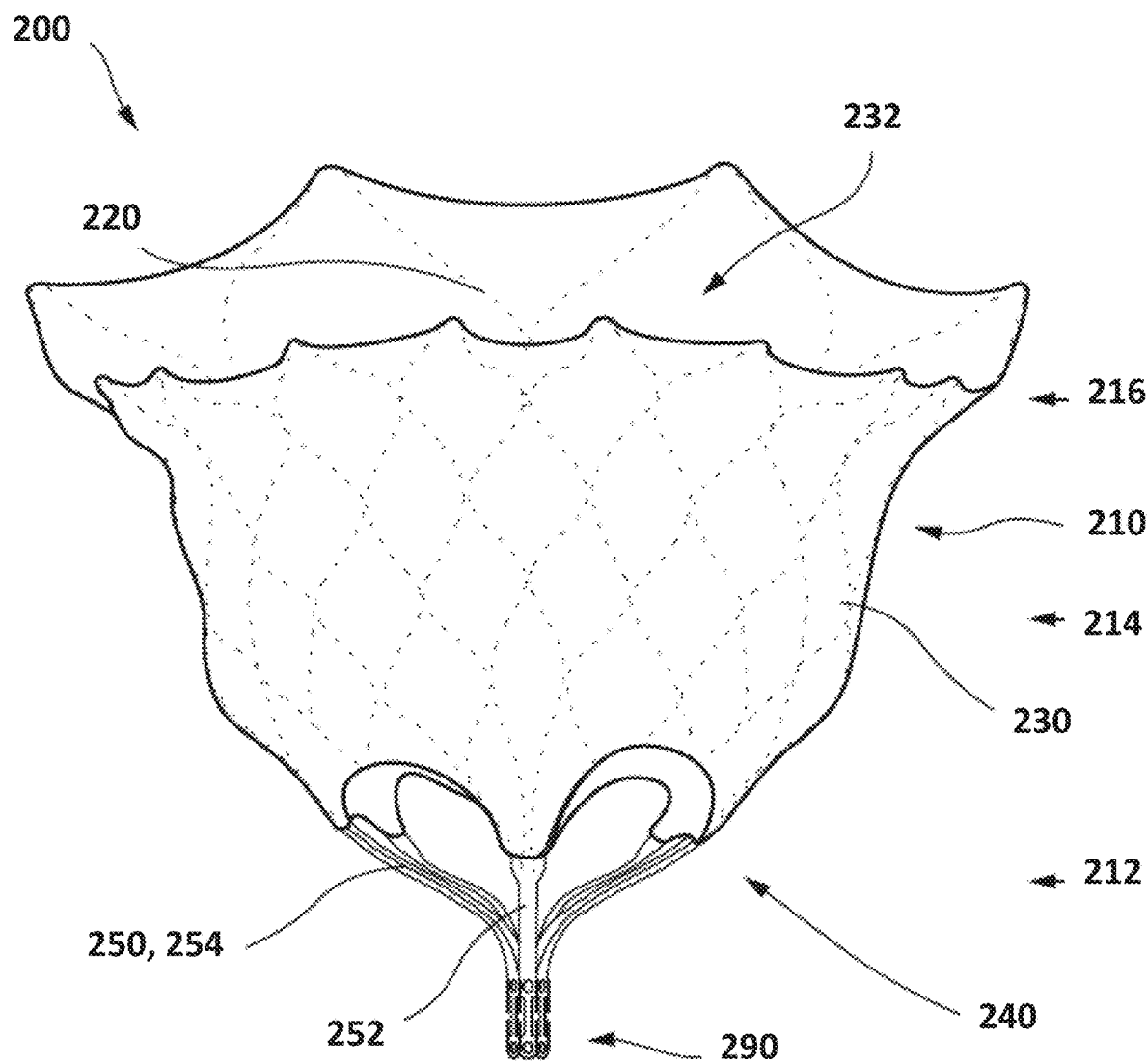
FIGS. 3-5 are front, bottom, and top views, respectively, of a prosthetic heart valve according to another embodiment.
Figure 4:
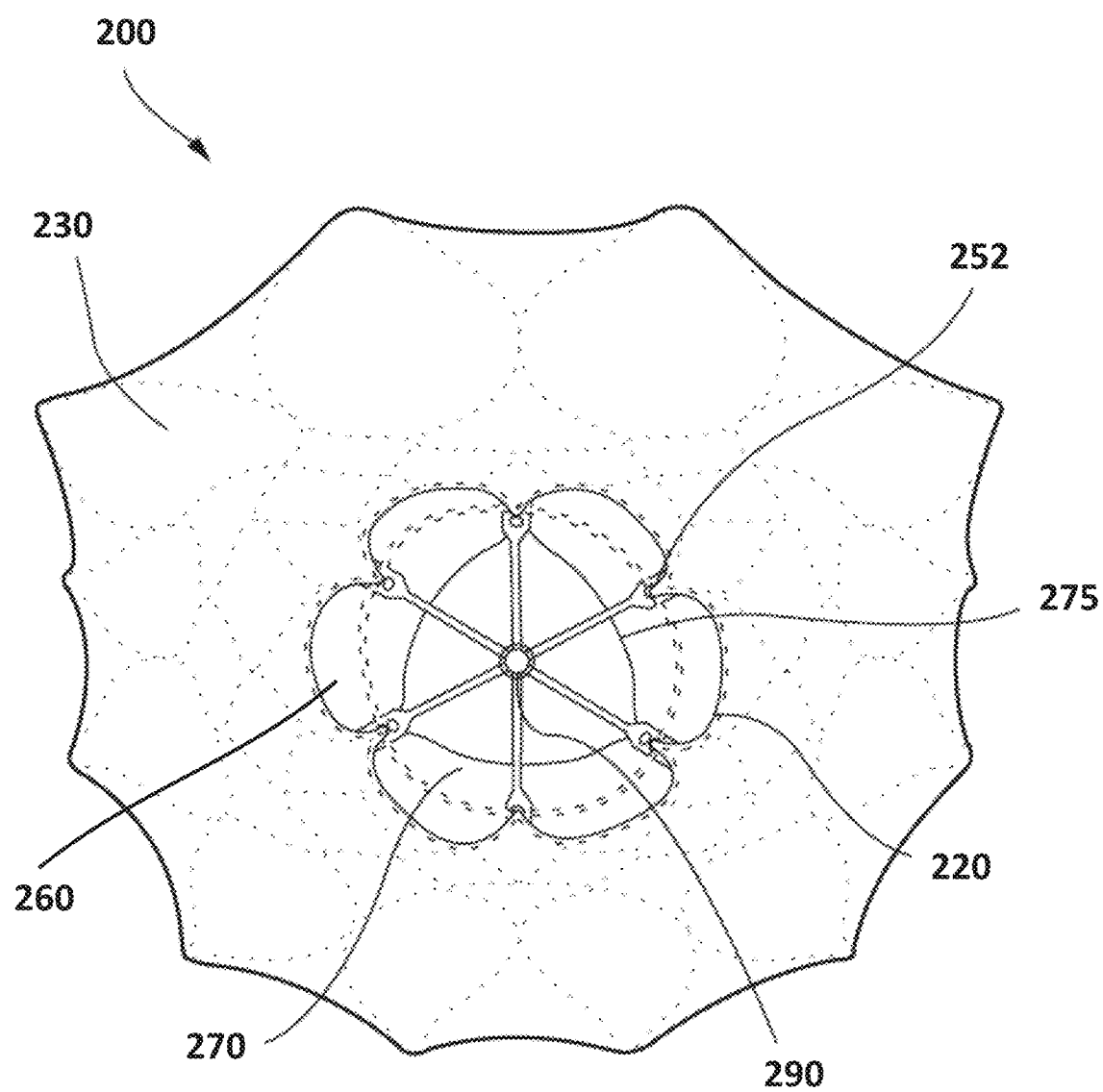
Figure 5:
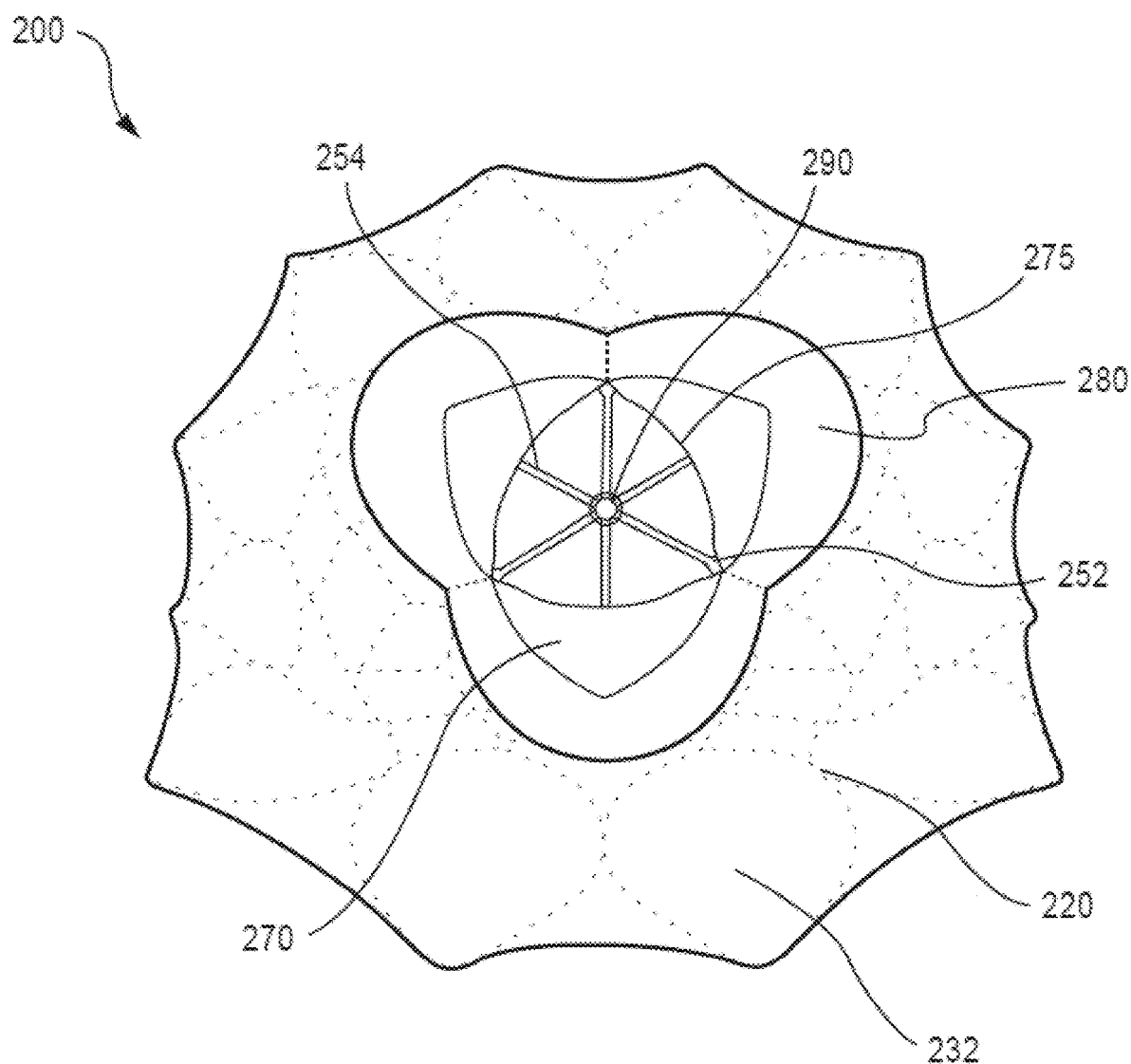

FIGS. 3-5 are front, bottom, and top views, respectively, of a prosthetic heart valve 200 according to an embodiment. Prosthetic heart valve 200 (also referred to herein as "valve" or "prosthetic valve") is designed to replace a damaged or diseased native heart valve such as a mitral valve. Valve 200 includes an outer frame assembly 210 and an inner valve assembly 240 coupled to the outer frame assembly 210.

As shown, outer frame assembly 210 includes an outer frame 220, covered on all or a portion of its outer face with an outer covering 230, and covered on all or a portion of its inner face by an inner covering 232. Outer frame 220 can provide several functions for prosthetic heart valve 200, including serving as the primary structure, as an anchoring mechanism and/or an attachment point for a separate anchoring mechanism to anchor the valve to the native heart valve apparatus, a support to carry inner valve assembly 240, and/or a seal to inhibit paravalvular leakage between prosthetic heart valve 200 and the native heart valve apparatus.

Outer frame 220 has a biased expanded configuration and can be manipulated and/or deformed (e.g., compressed and/or constrained) and, when released, return to its original unconstrained shape. To achieve this, outer frame 220 can be formed of materials, such as metals or plastics, that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 3, outer frame assembly 210 has an upper end (e.g., at the atrium portion 216), a lower end (e.g., at the ventricle portion 212), and a medial portion (e.g., at the annulus portion 214) therebetween. The upper end or atrium portion 216 (also referred to as "free end portion" or "open end portion") defines an open end portion of the outer frame assembly 210. The medial or annulus portion 214 of the outer frame assembly 210 has a perimeter that is configured (e.g., sized, shaped) to fit into an annulus of a native atrioventricular valve. The upper end of the outer frame assembly 210 has a perimeter that is larger than the perimeter of the medial portion. In some embodiments, the perimeter of the upper end of the outer frame assembly 210 has a perimeter that is substantially larger than the perimeter of the medial portion. As shown best in FIG. 5, the upper end and the medial portion of the outer frame assembly 210 has a D-shaped cross-section. In this manner, the outer frame assembly 210 promotes a suitable fit into the annulus of the native atrioventricular valve.

Inner valve assembly 240 includes an inner frame 250, an outer covering 260, and leaflets 270. As shown, the inner valve assembly 240 includes an upper portion having a periphery formed with multiple arches. The inner frame 250 includes six axial posts or frame members that support outer covering 260 and leaflets 270. Leaflets 270 are attached along three of the posts, shown as commissure posts 252 (best illustrated in FIG. 4), and outer covering 260 is attached to the other three posts, 254 (best illustrated in FIG. 4), and optionally to commissure posts 252. Each of outer covering 260 and leaflets 270 can be formed as described above for outer covering 160 and leaflets 170. For example, each of outer covering 260 and leaflets 270 can be formed of approximately rectangular sheets of material, which are joined together at their upper, or atrium end. The lower, ventricle end of outer covering 260 may be joined to inner covering 232 of outer frame assembly 210, and the lower, ventricle end of leaflets 270 may form free edges 275, though coupled to the lower ends of commissure posts 252.

Although inner valve assembly 240 is shown as having three leaflets, in other embodiments, an inner valve assembly can include any suitable number of leaflets. The leaflets 270 are movable between an open configuration and a closed configuration in which the leaflets 270 coapt, or meet in a sealing abutment.

Outer covering 230 of the outer frame assembly 210 and inner covering 232 of outer frame assembly 210, outer covering 260 of the inner valve assembly 240 and leaflets 270 of the inner valve assembly 240 may be formed of any suitable material, or combination of materials, such as those discussed above for valve 100. In this embodiment, the inner covering 232 of the outer frame assembly 210, the outer covering 260 of the inner valve assembly 240, and the leaflets 270 of the inner valve assembly 240 are formed, at least in part, of porcine pericardium. Moreover, in this embodiment, the outer covering 230 of the outer frame assembly 210 is formed, at least in part, of polyester.

Prosthetic valve 200 also defines a tapered annular space or pocket (not shown) formed between the outer surface of inner valve assembly 240 and the inner surface of outer frame assembly 210, open to the atrium end of valve assembly 200. As shown, a pocket closure or covering 280 (the pocket being disposed below pocket closure 280 in the top view of FIG. 5) is coupled along the periphery of the upper end of the inner valve assembly 240 and also to the outer valve assembly 210. In some embodiments, the pocket closure 280, or a portion thereof, can be coupled along any suitable portion of the inner valve assembly 240.

As discussed above, pocket closure 280 can be formed at least in part of any suitable material that is sufficiently porous to allow blood, including particularly red blood cells, to enter the pocket, but is not so porous as to allow undesirably large thrombi to leave the pocket. In this embodiment, pocket closure 280 is formed entirely of knit polyester (i.e., PET warp knit fabric) having apertures of about 90-120 microns. In some embodiments, a pocket closure can include apertures less than about 160 microns.

As previously described, in some embodiments, a prosthetic heart valve, such as a prosthetic mitral valve, can be configured to be moved to an inverted configuration for delivery of the prosthetic valve to within a heart of a patient. For example, the outer frame can be moved or inverted relative to the inner frame of the valve. After inverting the outer frame, the prosthetic valve can be inserted into a lumen of a delivery sheath such that the prosthetic valve is moved to a collapsed configuration for delivery of the valve o the heart. FIGS. 6A-6D and FIGS. 7A and 7B illustrate schematically an embodiment of a prosthetic valve that can be moved between a biased expanded configuration for use and an inverted configuration for delivery to a heart.

FIGS. 6A and 6B are schematic illustrations of a portion of a prosthetic heart valve 300, according to an embodiment, shown in a first configuration and a second configuration respectively, and FIGS. 6C and 6D illustrate the portions of the prosthetic heart valve 300 of FIGS. 6A and 6B, respectively, shown disposed within a lumen of a delivery sheath 326. FIGS. 7A and 7B illustrate a portion of the prosthetic heart valve 300 of FIGS. 6A and 6B, respectively, and show length dimensions for the prosthetic heart valve in each of the first configuration and the second configuration. The prosthetic heart valve 300 (also referred to herein as "prosthetic valve" or "valve") can be, for example, a prosthetic mitral valve. The valve 300 includes an outer frame 320 and an inner frame 350. The outer frame 320 and the inner frame 350 are each formed as a tubular structure. The outer frame 320 and the inner frame 350 can be coupled together at multiple coupling joints 346 disposed about a perimeter of the inner frame 350 and a perimeter of the outer frame 320 as described in more detail below. The valve 300 can also include other features, such as those described above with respect to FIGS. 1-5. For example, the valve 300 can include an outer frame assembly, including the outer frame 320, and an inner valve assembly that includes the inner frame 350, that can be formed or configured the same as or similar to the outer frame assemblies and inner valve assemblies described above with respect to FIGS. 1-5. For illustration purposes, only the inner frame 350 and the outer frame 320 are discussed with respect to FIGS. 6A-7B. The various characteristics and features of valve 300 described with respect to FIGS. 6A-7B can apply to any of the prosthetic valves described here.

The outer frame 320 is configured to have a biased expanded or undeformed shape and can be manipulated and/or deformed (e.g., compressed or constrained) and, when released, return to its original (expanded or undeformed) shape. For example, the outer frame 320 can be formed of materials, such as metals or plastics, that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used. The inner frame 350 can be formed from a laser-cut tube of Nitinol®. The inner frame 350 can also have a biased expanded or undeformed shape and can be manipulated and/or deformed (e.g., compressed and/or constrained) and, when released, return to its original (expanded or undeformed) shape. Further details regarding the inner frame 350 and the outer frame 320 are described below and with respect to valve 200 and FIGS. 3-5.

The valve 300 can be delivered and deployed within a left atrium of a heart using a variety of different delivery approaches including, for example, a transfemoral delivery approach, as described in the '572 PCT application, or a transatrial approach, as described in the '704 provisional application and the '221 application, or a transjugular approach as described, for example, in the '221 application. As described above, in some situations, such as when delivering a prosthetic valve to the heart via a transfemoral, transjugular or transatrial approach, because of the smaller size of the lumen of the delivery sheath, the size of the prosthetic valve during delivery should be sized accordingly. Thus, it is desirable to have a prosthetic valve that can be reconfigured between a biased expanded configuration for implantation in the heart (e.g., within a native mitral annulus) and a delivery configuration that has a smaller outer perimeter or profile to allow for delivery within the lumen of the delivery sheath. The prosthetic valve 300 and the embodiments of a prosthetic valve described herein can be constructed and formed to achieve these desired functions and characteristics.

More specifically, the valve 300 can have a biased expanded configuration (as shown in FIGS. 6A and 7A), an inverted configuration (as shown in FIGS. 6B and 7B), and a compressed or collapsed configuration (as shown in FIGS. 6C and 6D). The expanded configuration allows the valve 300 to function when implanted within the heart. The valve 300 can be moved to the inverted configuration and the compressed or collapsed configuration for delivery of the valve 300 to the heart of a patient.

To enable the valve 300 to be moved to the inverted configuration, the outer frame 320 can be coupled to the inner frame 350 in such a manner to allow the outer frame 320 to move relative to the inner frame 350. More specifically, the coupling joints 346 can couple the outer frame 320 to the inner frame 350 in such a manner to allow the outer frame 320 to be moved relative to the inner frame 350. For example, in some embodiments, the coupling joints 346 can be configured to allow the outer frame 320 to rotate about the coupling joint 346 relative to the inner frame 350. In some embodiments, coupling joints can provide a pivotal coupling between the outer frame 320 and the inner frame 350. In some embodiments, the coupling joints can provide a flexible attachment between the outer frame 320 and the inner frame 350. The coupling joints 346 can be a variety of different types and configurations as described herein with reference to the various embodiments of a prosthetic valve. For example, the coupling joints 146 can include a living hinge, a flexible member, sutures, a suture wrapped through an opening, a pin or tab inserted through an opening or any combinations thereof.

To move the valve 300 from the expanded configuration (FIG. 6A) to the inverted configuration (FIG. 6B), the outer frame 320 is moved to a prolapsed or inverted configuration relative to the inner frame 350, as shown in FIGS. 6B, 6D and 7B, by moving (e.g., rotating, pivoting, flexing) the outer frame 320 about the coupling joints 346. The elastic or superelastic structure of outer frame 320 of valve 300 also allows the outer frame 320 to be moved to, and disposed in, the prolapsed or inverted configuration relative to the inner frame 350. To move the outer frame 320 to the inverted configuration relative to the inner frame 350, the outer frame 320 is folded or inverted distally (to the right in FIG. 6B) relative to the inner frame 350 via the coupling joints 346. As shown in FIGS. 6A and 7A, the outer frame 320 is in a first position relative to the inner frame 350 prior to being inverted in which an open or free end portion 316 (also referred to the atrium portion 316 of the outer frame 320) is disposed proximally or to the left of the coupling joints 346 and in the same direction as a free end portion 347 (also referred to as a second end portion of the inner frame) of the inner frame 350. When the outer frame 320 is moved to an inverted configuration (i.e., second positon relative to the inner frame 350), the free end portion 316 is disposed distally of the coupling joints 346 (or to the right in FIGS. 6B and 7B) and in an opposite direction as the free end portion 347 of the inner frame 350. Said another way, when the valve 300 is in a biased expanded configuration (e.g., FIG. 6A), the coupling joints 346 are disposed between a first end portion 344 (also referred to as a tether coupling portion) of the inner frame 350 and the free end portion 316 of the outer frame 320. When the valve 300 is in the inverted configuration (e.g., FIG. 6B) (i.e., the outer frame 320 has been moved to an inverted configuration or position), the coupling joints 346 are disposed between the free end portion or second end portion 347 of the inner frame 350 and the free end portion 316 of the outer frame 320.

When in the inverted configuration, an overall length of the valve 300 is increased, but a length of the inner frame 350 and a length of the outer frame 320 remains the same (or substantially the same). For example, as shown in FIGS. 7A and 7B an overall length L1 of the valve 300 in the biased expanded configuration (prior to being inverted as shown in FIG. 7A) is less than the overall length L2 of the valve 300 when in the inverted configuration (FIG. 7B). A length Li of the inner frame 350 and a length Lo of the outer frame 320 is substantially the same (or the same) when the valve 300 is in both the biased expanded configuration and the inverted configuration. In addition, in some instances, depending on the specific configuration of the outer frame, an overall outer perimeter or outer diameter of the valve 300 can be smaller when the valve 300 is in the inverted configuration.

With the valve 300 in the inverted configuration, the valve 300 can be placed within a lumen of the delivery sheath 326 for delivery of the valve 300 to the left atrium of the heart, as shown in FIG. 6D. When placed within the lumen of the delivery sheath 326, the valve 300 is moved to the collapsed or compressed configuration in which the outer diameter or outer perimeter of the valve 300 is reduced. Because the valve 300 is in the inverted configuration, the valve 300 is able to be placed within a smaller delivery sheath 326 than would otherwise be possible. For example, for comparison purposes, FIG. 6C illustrates the valve 300 placed within a lumen of a delivery sheath 326' where the valve 300 has not been moved to an inverted configuration prior to being disposed within the delivery sheath 326'. As shown in FIG. 6C, an outer diameter of the valve 300 is reduced, but not to as small of a diameter as for the valve 100 when placed in a delivery sheath 326 when in the inverted configuration. Thus, in FIG. 6C, the valve 300 has an overall outer perimeter or outer diameter D1 and in FIG. 6D, the valve 300 has an overall outer perimeter or outer diameter D2, which is less than D1.

Thus, by disposing the outer frame 320 in the inverted configuration, the valve 300 can be collapsed into a smaller overall diameter, i.e. placed in a smaller diameter delivery sheath 326, than would be possible if the valve 300 were merely collapsed radially. This is because when the valve is in the biased expanded configuration, the inner frame 350 is nested within an interior of the outer frame 320, and thus the outer frame 320 must be collapsed around the inner frame 350. In some embodiments, the inner frame 350 and the outer frame are disposed concentrically. Whereas in the inverted configuration, the inner frame 350 and the outer frame 320 are arranged axially with respect to each other (i.e., the inner frame is not nested within the outer frame 350), such that the outer frame 320 can be collapsed without needing to accommodate all of the structure of the inner frame 350 inside it. In other words, with the inner frame 350 disposed mostly inside or nested within the outer frame 320, the layers or bulk of the frame structures cannot be compressed to as small a diameter. In addition, if the frames are nested, the structure is less flexible, and therefore, more force is needed to bend the valve, e.g. to pass through tortuous vasculature or to make tight turn in the left atrium after passing through the atrial septum to be properly oriented for insertion into the mitral valve annulus.

Figure 8A:
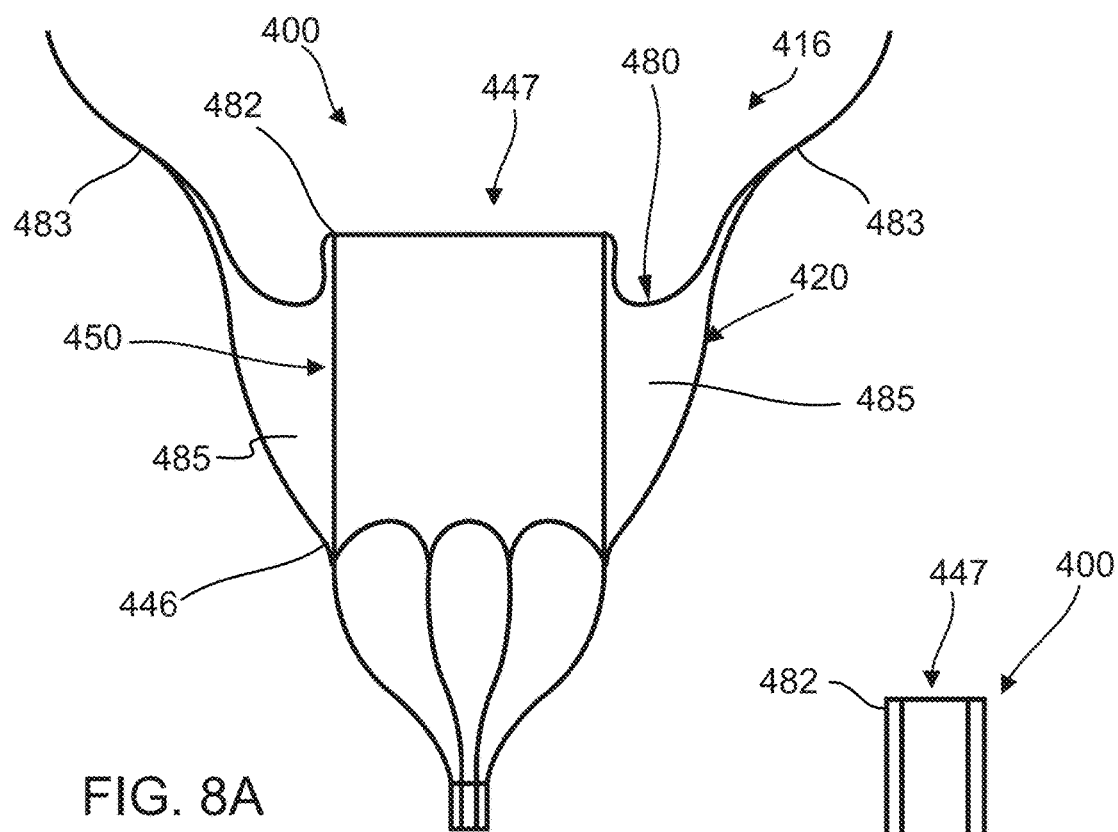
FIG. 8A is a front view of a prosthetic heart valve according to another embodiment, shown in a first configuration.
Figure 8B:
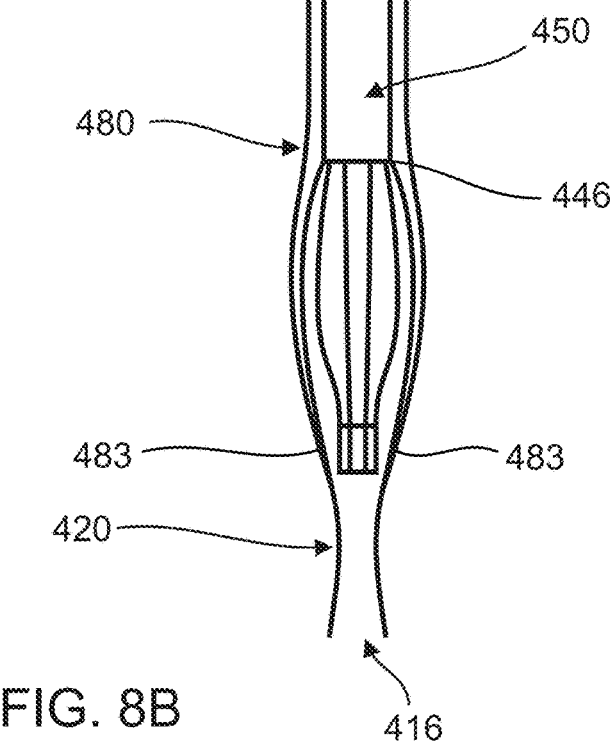
FIG. 8B is a front view of the prosthetic heart valve of FIG. 8A, shown in a second configuration.

FIGS. 8A and 8B illustrate another embodiment of a prosthetic heart valve that can be delivered and deployed within a left atrium of a heart using a variety of different delivery approaches and which can be moved between an expanded configuration and an inverted configuration as described above for valve 300. The prosthetic heart valve 400 (also referred to herein as "prosthetic valve" or "valve") can be, for example, a prosthetic mitral valve. The valve 400 includes an outer frame assembly including an outer frame 420 and an inner valve assembly including an inner frame 450. The outer frame 420 and the inner frame 450 are each formed as a tubular structure. The valve 400 can also include other features, such as those described above with respect to FIGS. 1A-7D. For illustration purposes, only the inner frame 450 and the outer frame 420 are discussed with respect to FIGS. 8A-8B. It should be understood that the various characteristics and features of the valves described above with respect to FIGS. 1A-7D can apply to valve 400.

The outer frame 420 and the inner frame 450 can be coupled together at multiple coupling joints 446 disposed about a perimeter of the inner frame 450 and a perimeter of the outer frame 420 as described above for valve 300. The coupling joints 446 can allow the outer frame 420 to be moved relative to the inner frame 450 as described above for valve 300. For example, the outer frame 420 can be moved between a first position (FIG. 8A) relative to the inner frame 450 to a second position (FIG. 8B) relative to the inner frame 450. In the first position, an open free end portion 416 of the outer frame 420 is disposed in the same direction as an open free end portion 447 of the inner frame 450 (see FIG. 8A). In the second position, the outer frame 420 is inverted relative to the inner frame 450 such that the free end portion 416 of the outer frame 420 is now disposed in an opposite direction as the free end portion 447 of the inner frame 450 (see FIG. 8B).

As described above for valves 100 and 200, a tapered annular space or pocket 485 (also referred to as "atrial pocket") is formed between an outer surface of the inner valve assembly and an inner surface of the outer frame assembly, open to an atrium end of valve 400. When valve 400 is disposed in the annulus of a native heart valve, blood from the atrium can move in and out of pocket 485. The blood can clot, forming thrombus. To enhance clotting, ingrowth of tissue into the surfaces of valve 400, and produce other benefits, the pocket 485 can be covered, or enclosed, by a pocket closure 480 (also referred to as an "atrial pocket closure"). The pocket closure 480 is coupled about a perimeter of the inner frame 450 and a perimeter of the outer frame 420 so as to close-out the pocket 485 at the atrial end of the valve 400. As shown in FIGS. 8A and 8B the pocket closure 480 is coupled to the inner frame 450 at coupling portion 482 and to outer frame 420 at coupling portion 483. The pocket closure 480 can be formed of one continuous segment or portion of material or can be formed with two or more portions or segments that are coupled together. For example, in some embodiments, the pocket closure 480 can be formed of three portions or segments that are sewn together with sutures or another suitable coupling method.

As described above, pocket closure 480 can be formed at least in part of any suitable material that is sufficiently porous to allow blood, including particularly red blood cells, to enter the pocket 485, but is not so porous as to allow undesirably large thrombi to leave the pocket 485. For example, pocket closure 480 may be formed at least in part from a material with apertures less than 160μ, and preferably between 90μ and 120μ. In this embodiment, the pocket closure 480 can be formed at least in part from a braided Nitinol material (or a braided tubular Nitinol material) that has the desired porosity. The braided Nitinol material also provides a desired stretchability, flexibility or deformability to accommodate movement of the outer frame 420 between the first positon relative to the inner frame 450 and the second inverted position relative to the inner frame 450. For example, the braided Nitinol material can have shape memory properties that allow the pocket closure 480 to be deformed and/or stretched and then revert back to an original shape or configuration when released.

As shown in FIG. 8A, when the outer frame 420 is in the first position relative to the inner frame 450, the pocket closure 480 is disposed in a first configuration. As shown in FIG. 8B, when the outer frame 420 is in the second position (i.e., inverted) relative to the inner frame 450, the pocket closure 480 is disposed in a second configuration. More specifically, when the outer frame 420 is moved to the second position in which the outer frame 420 is inverted relative to the inner frame 420, the material and structure of the pocket closure 480 enables the pocket closure 480 to stretch with the outer frame 420 as shown in FIG. 8B. In other words, as shown in FIG. 8B, the pocket closure 480 is stretched or elongated between where it is coupled to the inner frame (i.e., coupling portion 482) and where it is coupled to the outer frame (i.e., coupling portion 483) to a length greater than when the outer frame 420 is in the first positon as shown in FIG. 8A. When the outer frame 420 is moved back to the first position relative to the inner frame 450, the pocket closure 480 can assume its first configuration as shown in FIG. 8A.

Figure 9A:
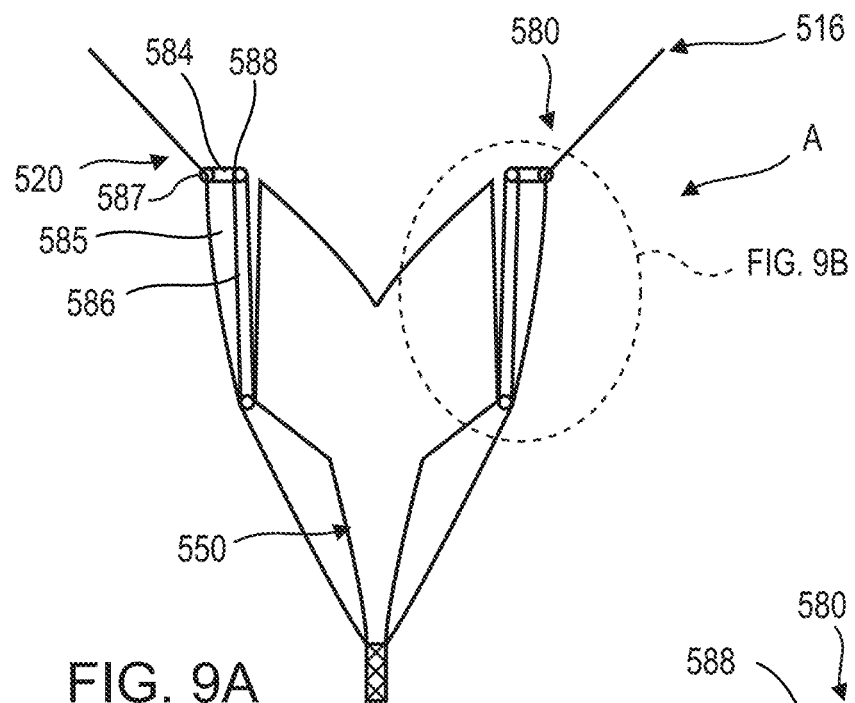
FIG. 9A is a front view of a prosthetic heart valve according to another embodiment, shown in a first configuration.
Figure 9B:
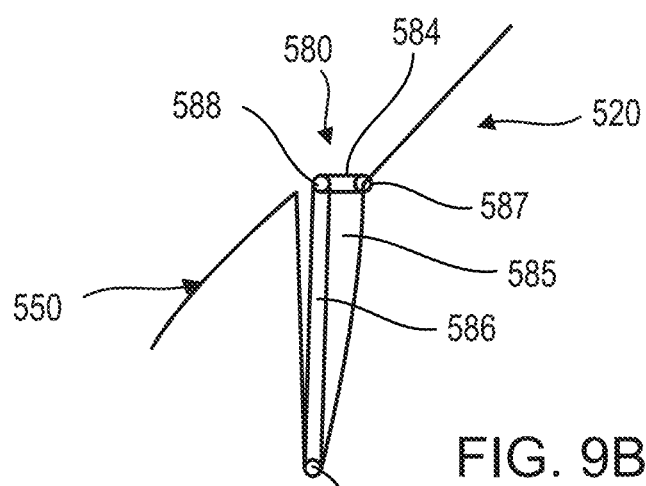
FIG. 9B is an enlarged view of encircled portion A of the prosthetic heart valve of FIG. 9A.
Figure 9C:
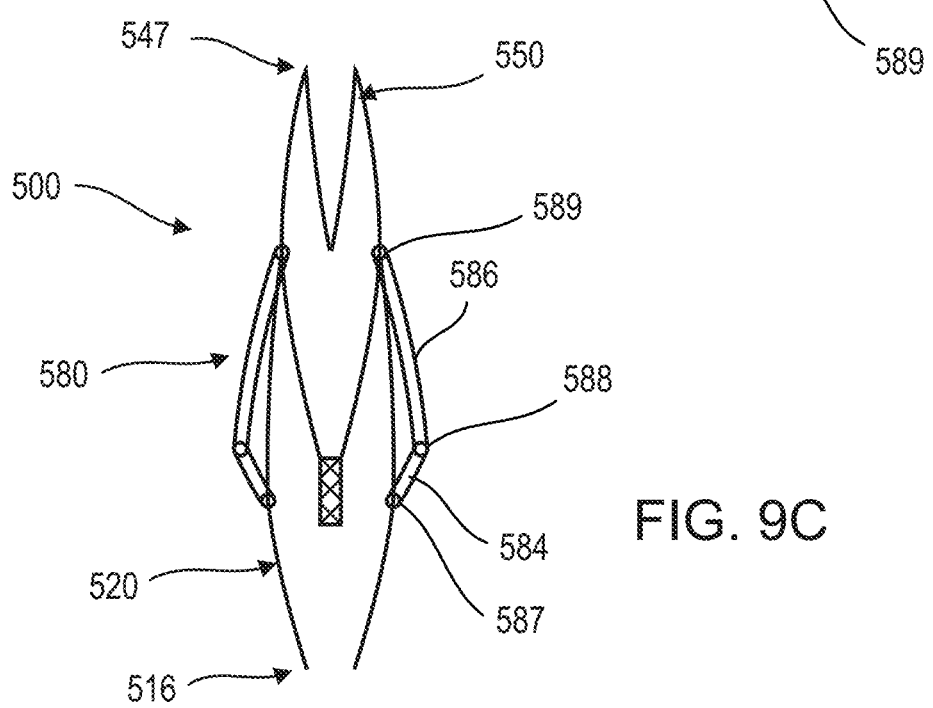
FIG. 9C is a front view of the prosthetic heart valve of FIG. 9A, shown in a second configuration.

FIGS. 9A and 9B illustrate another embodiment of a prosthetic heart valve that includes a pocket closure that can accommodate the valve being moved between an expanded configuration and an inverted configuration for delivery and deployment of the valve within a left atrium of a heart. The prosthetic heart valve 500 (also referred to herein as "prosthetic valve" or "valve") can be, for example, a prosthetic mitral valve. The valve 500 includes an outer valve assembly including an outer frame 520 and an inner valve assembly including an inner frame 550. The outer frame 520 and the inner frame 550 are each formed as a tubular structure. The valve 500 can also include other features, such as those described above with respect to FIGS. 1A-7D. For illustration purposes, only the inner frame 550 and the outer frame 520 are discussed with respect to FIGS. 8A-8B. It should be understood that the various characteristics and features of the valves described above with respect to FIGS. 1A-7D can apply to valve 500.

As with the previous embodiments, the outer frame 520 and the inner frame 550 can be coupled together at multiple coupling joints 546 disposed about a perimeter of the inner frame 550 and a perimeter of the outer frame 520 as described above for valve 300. The coupling joints 546 can allow the outer frame 520 to be moved relative to the inner frame 550 as described above for valve 300. For example, the outer frame 520 can be moved between a first position (FIG. 9A) relative to the inner frame 550 to a second position (FIG. 9B) relative to the inner frame 550. In the first position, an open free end portion 516 of the outer frame 520 is disposed in the same direction as an open free end portion 547 of the inner frame 550 (see FIG. 9A). In the second position, the outer frame 520 is inverted relative to the inner frame 550 such that the free end portion 516 of the outer frame 520 is now disposed in an opposite direction as the free end portion 547 of the inner frame 550 (see FIG. 9B).

As described above for valves 100 and 200, a tapered annular space or pocket 585 (also referred to as "atrial pocket") is formed between an outer surface of the inner valve assembly and an inner surface of the outer frame assembly, open to an atrium end of valve 500. When valve 500 is disposed in the annulus of a native heart valve, blood from the atrium can move in and out of pocket 585. The blood can clot, forming thrombus. To enhance clotting, ingrowth of tissue into the surfaces of valve 500, and produce other benefits, the pocket 585 can be covered, or enclosed, by a pocket closure 580 (also referred to as an "atrial pocket closure").

In this embodiment, the pocket closure 580 includes a first portion 584 coupled to a second portion 586. As shown in the detail view of FIG. 9B, the first portion 584 includes a first end coupled to the outer frame 520 at a coupling joint 587, and a second end coupled to the second portion 586 at a coupling joint 588. The second portion 586 has a first end coupled to the first portion 584 at the coupling joint 588 and a second end coupled to the outer frame 520 at a coupling joint 589. Thus, in this embodiment, the pocket closure 580 is coupled only to the outer frame 520. The pocket closure 580 can close-out the pocket at the atrial end of the valve 500. The first portion 584 and the second portion 586 of the pocket closure 580 can each be formed as one continuous segment or portion of material or can be formed with two or more portions or segments that are coupled together with for example, sutures or another suitable coupling method.

As described above, pocket closure 580 can be formed at least in part of any suitable material that is sufficiently porous to allow blood, including particularly red blood cells, to enter the pocket 585, but is not so porous as to allow undesirably large thrombi to leave the pocket 585. For example, pocket closure 580 may be formed at least in part from a material with apertures less than 160μ, and preferably between 90μ and 120μ. In this embodiment, the first portion 584 of pocket closure 580 can be formed at least in part from a woven or knit polyester fabric with apertures less than 160μ, and preferably between 90μ and 120μ. The second portion 586 of pocket closure 580 can be formed with a tubular braided Nitinol material as described above for valve 400 that can provide a desired stretchability or flexibility or deformability to accommodate the outer frame 520 moving between the first positon relative to the inner frame 550 and the second inverted position relative to the inner frame 550.

As shown in FIG. 9A, when the outer frame 520 is in the first position relative to the inner frame 550, the pocket closure 580 is disposed in a first configuration. As shown in FIG. 9B, when the outer frame 520 is in the second position (i.e., inverted) relative to the inner frame 550, the pocket closure 580 is disposed in a second configuration. More specifically, when the outer frame 520 is moved to the second position in which the outer frame 520 is inverted relative to the inner frame 520, the material and structure of the second portion 586 of the pocket closure 580 enables the pocket closure 580 to stretch with the outer frame 520 as shown in FIG. 9B. In other words, as shown in FIG. 9B, the second portion 586 of pocket closure 580 can stretch or elongate between where it is coupled to the first portion 584 of the pocket closure 580 (i.e., coupling joint 588) and where it is coupled to the outer frame 520 (i.e., coupling portion 589) to a length greater than when the outer frame 520 is in the first positon as shown in FIG. 9A. The first portion 584 of pocket closure 580 does not stretch when the outer frame 520 is moved to the second position (i.e., inverted) relative to the inner frame 550. When the outer frame 520 is moved back to the first position relative to the inner frame 550, the pocket closure 580 can assume its first configuration as shown in FIG. 9A.

Figure 10D:
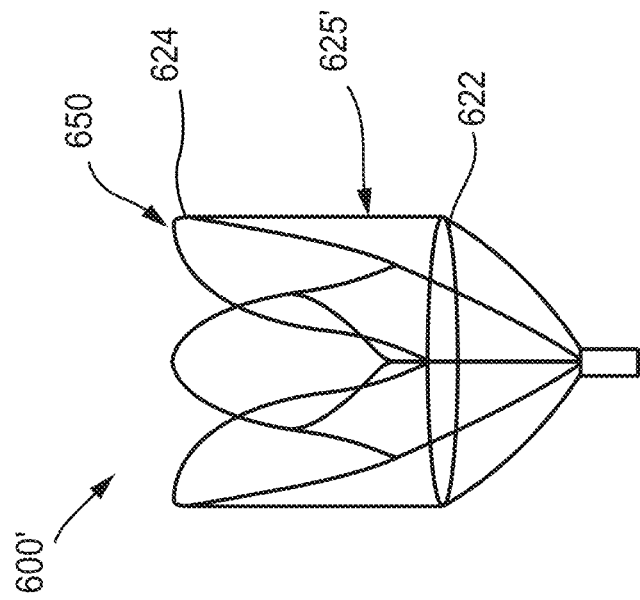
FIG. 10D is a perspective view of a prosthetic heart valve, according to another embodiment.
Figure 10C:
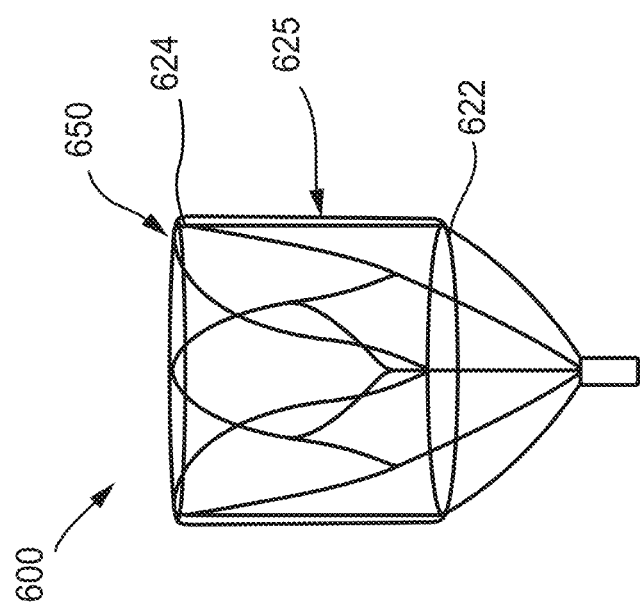
FIG. 10C is a perspective view of the prosthetic heart valve of FIG. 10A.

In some embodiments of a prosthetic heart valve, an additional material layer can be attached to the inner frame in addition to the outer covering described above for previous embodiments (e.g., outer covering 160). The additional material layer can be attached to an inner face or an outer face of the inner frame of the valve. For example, the additional material layer can be attached to an inner face of the inner frame and outside of the leaflets of the valve. In other words, the outer covering can be disposed between the leaflets and the additional material layer, with all three components (leaflets, outer covering and additional material layer) disposed on an inner side of the inner frame of the valve. The additional material layer may be desirable to prevent possible billowing of the belly area of the leaflet. Such billowing can occur, for example, when backpressure that can cause the leaflets to close also applies pressure to the belly area of the leaflets, potentially causing them to bulge out into the pocket area towards the outer frame. The additional material layer can be composed of a variety of different materials. FIGS. 10A-10C illustrate a prosthetic heart valve 600 that includes such a material layer 625. In this embodiment, the material layer 625 is disposed as a cylinder that covers an inner frame 650 from a base 622 of the inner frame 650 to a peak or atrium end 624 of the inner frame 650. As shown in FIGS. 10A and 10B, the valve 600 includes leaflets 670. As shown in FIG. 10C, the cylindrically disposed material layer 625 bridges the peaks 624 of the frame 650. In an alternative embodiment, the material layer can be configured to follow the shape of the inner frame as shown in FIG. 10D. In this embodiment, a valve 600' includes a material layer 625' that substantially follows or conforms to the shape of the inner frame 650. In other words, the material layer 625' spans between frame portions of the inner frame 650. In some embodiments, the material layers 625, 625' can be, for example, a polyester material.

While various embodiments have been described above, it should be understood that they have been presented by way of example only, and not limitation, and as such, various changes in form and/or detail may be made. Any portion of the apparatus and/or methods described herein may be combined in any suitable combination, unless explicitly expressed otherwise. The embodiments described herein can include various combinations and/or sub-combinations of the functions, components, and/or features of the different embodiments described.

Where methods described above indicate certain events occurring in certain order, the ordering of certain events and/or flow patterns may be modified. Additionally, certain events may be performed concurrently in parallel processes when possible, as well as performed sequentially.

What is claimed is:

1. A method of implanting a prosthetic heart valve into a native valve annulus, the method comprising:
   disposing the prosthetic heart valve within a delivery device in a collapsed delivery condition, the prosthetic heart valve including an inner frame having an open end portion, and an outer frame coupled to the inner frame and having an open end portion, the outer frame being inverted relative to the inner frame when the prosthetic heart valve is in the collapsed delivery condition so that the open end of the outer frame and the open end of the inner frame point in opposite directions;
   delivering the delivery device to the native valve annulus;
   ejecting the prosthetic heart valve from the delivery device;
   transitioning the prosthetic heart valve from the collapsed delivery condition to an expanded condition, the outer frame reverting relative to the inner frame during the transitioning so that the open end of the outer frame and the open end of the inner frame point in a same direction; and
   positioning the prosthetic heart valve in the native valve annulus,
   wherein in the expanded condition of the prosthetic heart valve, an annular space is defined between a portion of the inner frame and a portion of the outer frame, the annular space being open toward the open end portion of the outer frame and the open end portion of the inner frame when the prosthetic heart valve is in the expanded condition,
   a pocket covering being coupled to the inner frame and coupled to the outer frame such that the annular space is covered by the pocket covering between the open end portion of the inner frame and the open end portion of the outer frame when the prosthetic heart valve is in the expanded condition.

2. The method of claim 1, wherein the pocket covering is coupled to the inner frame and coupled to the outer frame when the prosthetic heart valve is in the collapsed delivery condition.

3. The method of claim 2, wherein the pocket covering is a stretchable pocket covering.

4. The method of claim 3, wherein the stretchable pocket covering has a first length when the prosthetic heart valve is in the collapsed delivery condition, and the stretchable pocket covering transitions to a second length smaller than the first length when the prosthetic heart valve transitions from the collapsed delivery condition to the expanded condition.

5. The method of claim 3, wherein the stretchable pocket covering, the inner frame, and the outer frame collectively define a pocket in which thrombus can form and be retained when the prosthetic heart valve is in the expanded condition and disposed within the native valve annulus of a patient.

6. The method of claim 5, wherein the pocket covering is formed of a material having a porosity that is sufficiently large to allow red blood cells to pass through the pocket closure into the pocket and that is sufficiently small to prevent thrombus formed from the red blood cells to pass through the pocket closure from the pocket.

7. The method of claim 1, wherein the pocket covering is formed of a braided Nitinol material.

8. The method of claim 1, wherein the prosthetic heart valve includes an outer covering disposed on the inner frame, a plurality of prosthetic leaflets disposed within an interior of the inner frame, and a material layer disposed over the outer covering and conforming to the shape of the inner frame, the material layer configured to prevent billowing of a belly area of the leaflets into the annular space.

9. The method of claim 1, wherein the outer frame is coupled to the inner frame at multiple coupling joints, the inner frame including a tether coupling portion opposite the open end portion of the inner frame, the coupling joints being disposed between the open end portion of the outer frame and the tether coupling portion of the inner frame when the prosthetic heart valve is in the expanded condition, the coupling joints being disposed between the open end portion of the inner frame and the open end portion of the outer frame when the prosthetic heart valve is in the collapsed delivery condition.

10. The method of claim 1, wherein the pocket covering has a first portion coupled to a second portion, the first portion being coupled to the outer frame at a first coupling joint, the second portion being coupled to the outer frame at a second coupling joint.

11. The method of claim 10, wherein the pocket covering is configured to move between a first configuration in which the second portion of the pocket covering has a first length and a second configuration in which the second portion of the pocket covering has a second length smaller than the first length as the prosthetic heart valve transitions from the collapsed delivery condition to the expanded condition.

12. The method of claim 10, wherein the pocket covering, the inner frame, and the outer frame collectively define a pocket in which thrombus can form and be retained when the prosthetic heart valve is in the expanded condition and disposed within the native valve annulus of a patient.

13. The method of claim 12, wherein the pocket closure is formed of a material having a porosity that is sufficiently large to allow red blood cells to pass through the pocket closure into the pocket and that is sufficiently small to prevent thrombus formed from the red blood cells to pass through the pocket closure from the pocket.

14. The method of claim 10, wherein the pocket covering is formed of a shape memory material configured to be to be moved from a biased configuration to an elongated configuration and back to the biased configuration.

15. The method of claim 1, wherein the pocket covering, the inner frame, and the outer frame collectively define a pocket in which thrombus can form and be retained when the prosthetic heart valve is in the expanded condition and disposed within the native valve annulus of a patient.

16. The method of claim 15, wherein the pocket closure is formed of a material having a porosity that is sufficiently large to allow red blood cells to pass through the pocket closure into the pocket and that is sufficiently small to prevent thrombus formed from the red blood cells to pass through the pocket closure from the pocket.

17. The method of claim 1, wherein ejecting the prosthetic heart valve from the delivery device includes ejecting the inner frame from the delivery device after the outer frame is ejected from the delivery device.

18. The method of claim 17, wherein the inner frame retains a same orientation relative to the delivery device as the inner frame is ejected from the delivery device.

19. The method of claim 18, wherein the outer frame reverses orientation relative to the delivery device as the outer frame is ejected from the delivery device.

20. The method of claim 1, wherein delivering the delivery device to the native valve annulus includes passing the delivery device from a right atrium to a left atrium through an atrial septum disposed between the right atrium and the left atrium.

* * * * *